(12) United States Patent
Kamei

(10) Patent No.: US 10,098,831 B2
(45) Date of Patent: Oct. 16, 2018

(54) SURFACE-TREATED POWDER AND COSMETIC HAVING THE SAME

(71) Applicant: SHIN-ETSU CHEMICAL CO., LTD., Tokyo (JP)

(72) Inventor: Masanao Kamei, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 44 days.

(21) Appl. No.: 15/103,391

(22) PCT Filed: Nov. 28, 2014

(86) PCT No.: PCT/JP2014/081569
§ 371 (c)(1),
(2) Date: Jun. 10, 2016

(87) PCT Pub. No.: WO2015/093258
PCT Pub. Date: Jun. 25, 2015

(65) Prior Publication Data
US 2016/0303032 A1    Oct. 20, 2016

(30) Foreign Application Priority Data

Dec. 17, 2013 (JP) ................. 2013-260447

(51) Int. Cl.
| | | |
|---|---|---|
| *A61K 8/893* | (2006.01) | |
| *A61Q 1/02* | (2006.01) | |
| *A61K 8/27* | (2006.01) | |
| *A61K 8/29* | (2006.01) | |
| *A61K 8/19* | (2006.01) | |
| *A61Q 17/04* | (2006.01) | |
| *A61K 8/89* | (2006.01) | |
| *A61K 8/91* | (2006.01) | |
| *A61K 8/895* | (2006.01) | |
| *A61K 8/06* | (2006.01) | |
| *A61K 8/02* | (2006.01) | |

(Continued)

(52) U.S. Cl.
CPC ............. *A61K 8/893* (2013.01); *A61K 8/022* (2013.01); *A61K 8/0241* (2013.01); *A61K 8/062* (2013.01); *A61K 8/064* (2013.01); *A61K 8/19* (2013.01); *A61K 8/27* (2013.01); *A61K 8/29* (2013.01); *A61K 8/89* (2013.01); *A61K 8/895* (2013.01); *A61K 8/91* (2013.01); *A61K 8/92* (2013.01); *A61Q 1/02* (2013.01); *A61Q 17/04* (2013.01); *A61Q 19/00* (2013.01); *C08K 3/22* (2013.01); *C08L 83/04* (2013.01); *C08L 83/06* (2013.01); *A61K 2800/10* (2013.01); *A61K 2800/592* (2013.01); *A61K 2800/624* (2013.01); *A61K 2800/651* (2013.01); *A61Q 5/12* (2013.01); *A61Q 15/00* (2013.01); *C08K 2003/2241* (2013.01); *C08K 2003/2296* (2013.01)

(58) Field of Classification Search
None
See application file for complete search history.

(56) References Cited

U.S. PATENT DOCUMENTS 6,576,623 B1    6/2003    Nakanishi et al.
6,660,281 B1    12/2003   Nakanishi et al.
(Continued)

FOREIGN PATENT DOCUMENTS

CN    101260190 A    9/2008
JP    2719303 B2     2/1998
(Continued)

OTHER PUBLICATIONS

Lee et al., "Preparation, characterization, and thermal properties of alt-copoly[1,9-decaphenylpentasiloxanylene/1,3-bis(ethylene)permethyloligosiloxanylene]s", Journal of Polymer Science: Part A: Polymer Chemistry, 43, 2005, pp. 6146-6152.*
(Continued)

*Primary Examiner* — Melissa L Fisher
(74) *Attorney, Agent, or Firm* — Oliff PLC

(57) ABSTRACT

Provided is a surface-treated powder, where at least one compound of general formula (1) adheres to the surface of the powder. In formula (1), $R^2$ is a monovalent aromatic hydrocarbon group having 6-12 carbon atoms, $R^4$ is a monovalent non-aromatic hydrocarbon group having 1-30 carbon atoms, $R^1$ and $R^0$ are a group selected from aforementioned groups defined for $R^2$ and $R^4$, and $R^3$ is a group of formula (2), $R^5$ is a divalent hydrocarbon group having 2 to 8 carbon atoms and $R^6$ is an alkyl group having 1 to 6 carbon atoms, a, b, c, and d are integers of from 0-3, 0-200, 1-150, and 0-50, respectively, provided that when a is 0, d and e are integers of from 1-50 and 0-2, respectively, and c/(b+c+d) is 0.25 or more.

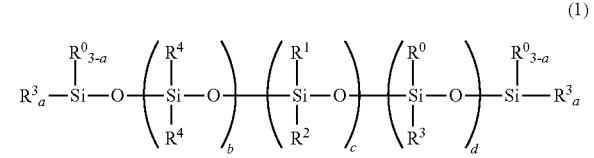

(1)

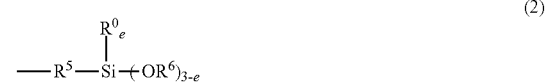

(2)

13 Claims, No Drawings

(51) Int. Cl.
*A61K 8/92* (2006.01)
*A61Q 19/00* (2006.01)
*C08L 83/04* (2006.01)
*C08L 83/06* (2006.01)
*C08K 3/22* (2006.01)
*A61Q 5/12* (2006.01)
*A61Q 15/00* (2006.01)

(56) References Cited

U.S. PATENT DOCUMENTS

| | | |
|---|---|---|
| 7,722,899 B2 | 5/2010 | Ono et al. |
| 2004/0156809 A1 | 8/2004 | Ono et al. |
| 2006/0034875 A1* | 2/2006 | Nakanishi .............. A61K 8/891 424/401 |

FOREIGN PATENT DOCUMENTS

| | | |
|---|---|---|
| JP | 2001-039819 A | 2/2001 |
| JP | 3450541 B2 | 9/2003 |
| JP | 3567335 B2 | 9/2004 |
| JP | 3736848 B2 | 1/2006 |
| JP | 3912961 B2 | 5/2007 |
| JP | 2007-153751 A | 6/2007 |
| KR | 10-2001-0007568 A | 1/2001 |

OTHER PUBLICATIONS

May 29, 2017 Office Action issued in European Search Report issued in 14872340.6.
Feb. 17, 2015 International Search Report issued in International Patent Application No. PCT/JP2014/081569.

* cited by examiner

SURFACE-TREATED POWDER AND COSMETIC HAVING THE SAME

FIELD OF THE INVENTION

The present invention relates to surface-treated powder and a cosmetic comprising the same. Specifically, the present invention relates to surface-treated powder which give a cosmetic which forms a uniform cosmetic film having excellent adhesiveness, and a cosmetic which does not run with time, is not sticky, gives a good feeling in use, in which the powder disperses stably with time.

BACKGROUND OF THE INVENTION

Secretions from human, such as sweat, tears and sebum, cause makeup to run. Particularly, for sunscreen agents and make-up cosmetics, secretion such as sebum from a skin, besides oil blended in the cosmetics, excessively wet powder in cosmetics. This is a major factor for the makeup to run. Further, friction is one of external factors of the makeup to run. Therefore, the surface of powder is hydrophobized with a reactive silicone, a silane coupling agent or a fluorine compound to improve water- and oil-repellency of the powder, whereby durability of cosmetics is improved.

An oil mixture of silicone oils, hydrocarbon oils, ester oils and glyceride oils is often used as an oil agent for cosmetics containing powder in order to improve its feel or compatibility with other components. Further, a highly polar organic ultraviolet absorbent is contained in cosmetics having an ultraviolet absorbing effect. Then, the cosmetics have worse uniformity as a whole of solution or dispersion and, accordingly, worse stability with time, such that the oils separate or powder settles.

In order to solve the aforesaid problems, Patent Literature 1 describes a cosmetic comprising an alkyl-modified organopolysiloxanes having a long alkyl chain, and methyl trimethicone. Patent Literature 2 describes a cosmetic comprising a silicone having a long chain alkyl group and a polyoxyethylene group. In these cosmetics, the oil component is stably suspended, but the powder is not enough stably suspended.

Patent Literature 3 describes a make-up cosmetic comprising modified powder obtained by coating the surface of powder with methyl hydrogen polysiloxane and heating the powder. However, when the methylhydrogenpolysiloxane type surface treating agent, such as methylhydrogenpolysiloxane and dimethylmethylhydrogenpolysiloxane is adopted, unreacted Si—H groups remain on the surface of the powder. Accordingly, when the powder is added in a cosmetic, there is a problem that hydrogen gas generates, depending on a property of liquid. Patent Literature 4 describes a cosmetic comprising pigments treated with an organic silicon compound, wherein a one-terminal alkoxy-modified linear silicone is orientation-adsorbed on the surface of the pigment and heat treated. However, the one-terminal alkoxy-modified silicone has less points reactive with powder, compared to the methylhydrogenpolysiloxane type treating agent, so that untreated surface remains in the powder. Therefore, when the powder treated with the one-terminal alkoxy-modified silicone is used in a pressed powder cosmetic, the treatment effect is not sufficiently obtained in a solution system.

Further, Patent Literature 5 describes powder surface-treated with an acrylic/silicone copolymer having a hydrolyzable silyl group. Patent Literature 6 describes a silicone treating agent for powder which has a silicone chain having a branched structure and a hydrolyzable alkoxy group. Patent Literature 7 describes a water-repellent cosmetic powder obtained by treating powder with a carboxyl group-containing organopolysiloxane. These surface-treated powders have excellent water- and oil-repellency. However, when these powders are used in a cosmetic comprising a highly polar oil, such as an ester oil and an organic ultraviolet absorbent, there are problems such that the powder settles with time, color of a coating film is uneven and a color irregularity occurs and, therefore, these powders are not satisfactory.

PRIOR LITERATURES

Patent Literature 1: Japanese Patent Application Laid-Open No. 2007-153751
Patent Literature 2: Japanese Patent Application Laid-Open No. 2001-039819
Patent Literature 3: Japanese Patent No. 2719303
Patent Literature 4: Japanese Patent No. 3567335
Patent Literature 5: Japanese Patent No. 3736848
Patent Literature 6: Japanese Patent No. 3912961
Patent Literature 7: Japanese Patent No. 3450541

SUMMARY OF THE INVENTION

Problems to be Solved by the Invention

One of the purposes of the present invention is to provide a cosmetic which has excellent adhesiveness, forms a uniform cosmetic film which has no color unevenness and a good coloring property, does not cause makeup to run with time, is not sticky, gives a good feeling in use, shows stable dispersion of powder, and the powder in which disperse stably with time. In particular, the purposes of the present invention are to attain the aforesaid effects even in a cosmetic comprising a mixture of a silicone oil and a polar oil.

Means to Solve the Problems

The present inventor has made research to solve the aforesaid problems and found that powder surface-treated with a hydrolysable group containing-reactive silicone compound having a specific structure is well compatible with various oil and that a cosmetic comprising the surface-treated powder and oil solves the aforesaid problems.

Thus, the present invention provides surface-treated powder, wherein at least one compound represented by the following general formula (1) adheres to the surface of the powder, (1)

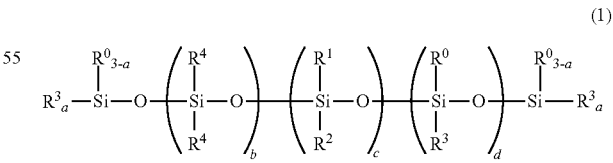

wherein $R^2$ is, independently of each other, a monovalent aromatic hydrocarbon group having 6 to 12 carbon atoms, $R^4$ is, independently of each other, a substituted or unsubstituted, monovalent non-aromatic hydrocarbon group having 1 to 30 carbon atoms, $R^1$ and $R^0$ are, independently of each other, a group selected from aforementioned groups defined for $R^2$ and $R^4$, and $R^3$ is, independently of each other, a group represented by the following formula (2):

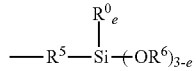
(2)

wherein $R^0$ is as defined above, $R^5$ is a divalent hydrocarbon group having 2 to 8 carbon atoms and $R^6$ is an alkyl group having 1 to 6 carbon atoms,
a is an integer of from 0 to 3, b is an integer of from 0 to 200, c is an integer of from 1 to 150, d is an integer of from 0 to 50, provided that when a is 0, d is an integer of from 1 to 50, e is an integer of from 0 to 2 and $c/(b+c+d)$ is 0.25 or more, and the parenthesized siloxane units may bond randomly or form a block unit.

Further, the present invention provides a cosmetic comprising the surface-treated powder and oil.

Effects of the Invention

The cosmetic comprising the present surface-treated powder has an excellent adhesiveness and forms a uniform cosmetic film which has no color unevenness and a good coloring property. The present cosmetic does not cause makeup to run with time, is not sticky, and gives a good feeling in use. Further, dispersion of the powder is stable and provides a cosmetic which changes less with time. These effects can be achieved even in a cosmetic comprising a mixture of a silicone oil and a polar oil. Accordingly, the surface-treated powder of the present invention can be successfully used in cosmetics.

DETAILED DESCRIPTION OF THE INVENTION

The present invention will be described below in detail.
(A) Surface-Treated Powder
The first aspect of the present invention provides surface-treated powder, wherein at least one compound represented by the following general formula (1) adheres to the surface of the powder.

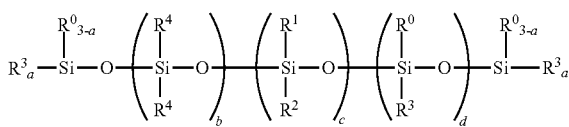
(1)

wherein $R^2$ is, independently of each other, a monovalent aromatic hydrocarbon group having 6 to 12 carbon atoms, $R^4$ is, independently of each other, a substituted or unsubstituted, monovalent non-aromatic hydrocarbon group having 1 to 30 carbon atoms, $R^1$ and $R^0$ are, independently of each other, a group selected from aforementioned groups defined for $R^2$ and $R^4$, and $R^3$ is, independently of each other, a group represented by the following formula (2):

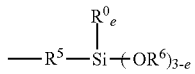
(2)

wherein $R^0$ is as defined above, $R^5$ is a divalent hydrocarbon group having 2 to 8 carbon atoms and $R^6$ is an alkyl group having 1 to 6 carbon atoms,
a is an integer of from 0 to 3, b is an integer of from 0 to 200, c is an integer of from 1 to 150, d is an integer of from 0 to 50, provided that when a is 0, d is an integer of from 1 to 50, e is an integer of from 0 to 2 and $c/(b+c+d)$ is 0.25 or more, and the parenthesized siloxane units may bond randomly or form a block unit.

In the aforesaid formula (1), $R^4$ is a substituted or unsubstituted, monovalent non-aromatic hydrocarbon group having 1 to 30 carbon atoms, preferably a group selected from the groups consisting of alkyl groups having 1 to 30 carbon atoms, cycloalkyl groups having 4 to 10 carbon atoms, and halogen-substituted alkyl groups having 1 to 15 carbon atoms. Examples of $R^4$ includes alkyl group such as methyl, ethyl, propyl, butyl, pentyl, hexyl, heptyl, octyl, nonyl, decyl and stearyl groups; cycloalkyl groups such as cyclopentyl and cyclohexyl group; or those groups where a part or the whole of their hydrogen atoms are replaced with a halogen atom(s), such as fluorine, chlorine, bromine, and iodine atoms. The fluorine-substituted groups includes, for instance, fluorine-substituted alkyl groups such as a trifluoropropyl group and a heptadecafluorodecyl group. Among these, an alkyl group having 1 to 15 carbon atoms is preferred.

In the aforesaid formula (1), $R^2$ is a monovalent aromatic hydrocarbon group having 6 to 12 carbon atoms, preferably a phenyl group, an ethyl phenyl group or a propylphenyl group. Among these, a phenyl group and a propylphenyl group are preferred.

In the aforesaid formulas (1) and (2), $R^1$ and $R^0$ are, independently of each other, a group selected from aforementioned groups defined for $R^2$ and $R^4$. Preferably, $R^1$ is an alkyl group having 1 to 15 carbon atoms or a phenyl group, and $R^0$ is an alkyl group having 1 to 15 carbon atoms.

In the aforesaid formula (2), $R^5$ is a divalent hydrocarbon group having 2 to 8 carbon atoms, preferably 2 to 6 carbon atoms. Examples of $R^5$ include ethylene, propylene and hexamethylene groups. $R^6$ is an alkyl group having 1 to 6 carbon atoms. Examples of $R^6$ include methyl, ethyl, propyl, isopropyl and hexyl groups. Among these, methyl and ethyl groups are preferred.

a is an integer of from 0 to 3, preferably 0 or 1. b is an integer of from 0 to 200, preferably an integer of from 0 to 100. c is an integer of from 1 to 150, preferably an integer of from 1 to 100. d is an integer of from 0 to 50, provided that when a is 0, d is an integer of from 1 to 50, preferably 1 to 20. e is an integer of from 0 to 2, preferably 0 or 1. $c/(b+c+d)$ is 0.25 or more, preferably 0.25 or more to 0.80 or less. If the value of $c/(b+c+d)$ is less than the aforesaid lower limit, when a polar oil such as glyceride oils and an organo ultraviolet absorbent is added in a cosmetic, an oil phase separates or powder settles out with time, because of less compatibility of the oil.

The compound represented by the formula (1) may be used singly or in combination of two or more of them. For instance, the compound is such represented by the following formulas.

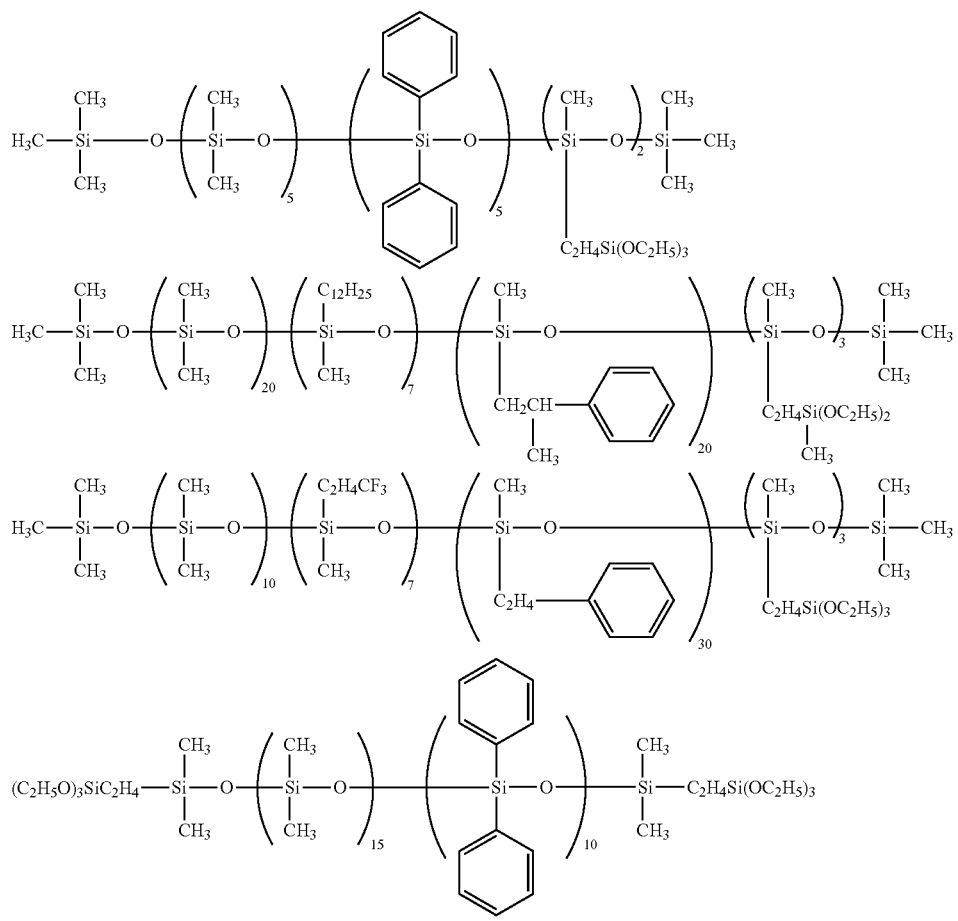

Powder to be surface-treated with the aforesaid compound may be one which is commonly used in cosmetics, regardless of a shape such as spherical, spindle, acicular, fan-like and plate-like; a particle size such as fume size, fine particle and pigment size; and particle structure such as porous and non-porous. Examples of the powder include powder of metal salt surfactant, colored pigments, pearl pigments, metal powder pigments, natural colors, and other inorganic or organic powder.

Examples of the powder of metal salt surfactant (so-called metal soap) include zinc stearate, aluminum stearate, calcium stearate, magnesium stearate, zinc myristate, magnesium myristate, zinc cetyl phosphate, calcium cetyl phosphate, zinc/sodium cetyl phosphate, zinc palmitate, aluminum palmitate and zinc laurate.

Examples of the colored pigments include inorganic red pigments such as iron oxide, iron hydroxide, and iron titanate; inorganic brown pigments such as γ-iron oxide; inorganic yellow pigments such as iron oxide yellow and loess; inorganic black pigments such as iron oxide black and carbon black; inorganic violet pigments such as manganese violet and cobalt violet; inorganic green pigments such as chromium hydroxide, chromium oxide, cobalt oxide, and cobalt titanate; inorganic blue pigments such as prussian blue and ultramarine blue; lakes of tar pigments, lakes of natural dyes, and synthetic resin powder such as a composite of these powder.

Examples of the pearl pigments include titanium oxide-coated mica, titanium oxide-coated mica, bismuth oxychloride, titanium oxide-coated bismuth oxychloride, titanium oxide-coated talc, fish scales, and titanium oxide-coated colored mica.

Examples of the metal powder pigments include aluminum powder, copper powder and stainless steel powder. Examples of the tar pigments include Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, and Orange No. 207.

Examples of the natural pigments include carminic acid, laccaic acid, carthamin, brazilin, and crocin. Powder which absorbes and scatters ultraviolet, such as titanium oxide fine particles, iron-containing titanium oxide fine particles, zinc oxide fine particles, cerium oxide fine particles and complex of these.

Examples of the other inorganic powder include titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, muscovite, synthetic mica, phlogopite, lepidolite, biotite, lithia mica, silicic acid, silicic anhydride, aluminum silicate, magnesium silicate, aluminum magnesium silicate, calcium silicate, barium silicate, strontium silicate, metal salts of tungstenic acid, hydroxyapatite, vermiculite, higilite, bentonite, montmorillonite, hectoliter, zeolite, ceramics powder, calcium secondary phosphate, alumina, aluminum hydroxide, boron nitride, boron nitride, silica, glass and silylated silica. Among these, preferred are zinc oxide, titanium oxide and extender pigments such as mica, sericite, talc and kaolin.

Examples of the other organic powder include polyamide powder, poly-acrylic acid/acrylic ester powder, polyester powder, polyethylene powder, polypropylene powder, polystyrene powder, polyurethane powder, benzoguanamine powder, polymethylbenzoguanamine powder, tetrafluoroethylene powder, polymethylmethacrylate powder, cellulose powder, silk powder, nylon powder such as Nylon 6 and Nylon 12, crosslinked silicone fine powder of crosslinked dimethylsilicone, fine powder of polymethylsylsesquioxane, fine powder of spherical crosslinked-organopolysiloxane elastomer coated with polymethylsylsesquioxane, hydrophobized silica, styrene/acrylic acid copolymer, divinylbenzene/styrene copolymer, vinyl resin, urea resin, phenol resin, fluoro resin, silicone resin, acrylic resin, melamine resin, epoxy resin, polycarbonate resin, microcrystalline fiber powder, starch powder, fatty acid and starch derivant powder and lauroyl lysine.

A weight ratio of the aforesaid compound represented by the formula (1) to the powder is preferably 0.1 to 30 parts by weight, particularly 0.5 to 20 parts by weight, relative to 100 parts by weight of the powder.

Surface treatment of the powder with the aforesaid compound represented by the formula (1) may be done in any conventional manner and is not limited. For instance, the following methods may be used.

1. Mixing the powder and the compound, followed by treatment with a crusher such as a ball mill, a bead mill, a jet mill and a high pressure homogenizer.
2. Dispersing the powder in a solvent comprising the compound to let the compound to be adsorbed on the surface of the powder, followed by drying and sintering.
3. Dispersing the powder in water to prepare a slurry, adding the compound or an emulsion of the compound thereto with stirring to let the compound to be adsorbed on the surface of the powder, followed by drying and sintering.

Further, other known surfactants such as silicone compounds other than the aforesaid compound represented by the formula (1), fluorine compounds, silane coupling agents and amino acids may be used, in addition to the aforesaid compound represented by the formula (1), in order to treat the surface of the powder.

The second aspect of the present invention is a cosmetic comprising (A) the surface-treated powder and (B) oil. An amount of the surface-treated powder (A) in the cosmetic may be properly selected depending on a form of the cosmetic. In particular, the amount of the surface-treated powder is 1 to 95 weight %, preferably 1 to 50 weight %, based on total weight of the cosmetic. When the cosmetic is in a powder form, the amount of the surface-treated powder is preferably 70 to 95 weight %.

(B) Oil

Any oil which is commonly used in cosmetics may be used, such as and solid oil, semisolid oil and liquid oil. The oil may be used singly or in combination of two or more kinds of oil. An amount of the oil (B) in the present cosmetic may be properly selected depending on a form of the cosmetic. In particular, the amount of the oil is 1 to 70 weight %, preferably 1 to 50 weight %, based on total weight of the cosmetic.

The present component (B) preferably comprises a polar oil having an IOB of 0.05 to 1, further preferably 0.1 to 0.85.

When the value of IOB is in the aforesaid range, the dispersion stability of the surface-treated powder is better. Here, the IOB is an abbreviation for Inorganic/Organic Balance. This is an index indicating the balance between hydrophilicity and lipophilicity and the value is calculated by the following formula: IOB=Inorganic Value (IV)/Organic Value (OV). The inorganic value and the organic value are based on an organic conceptual diagram. The organic conceptual diagram was proposed by Atsushi Fujita and described in detail in "Fragrance Journal", vol. 50, pp. 79-82 (1981), "Organic Conceptual Diagram—Fundamentals and Applications, Yoshio Koda, Sankyo Publishing, 1984. The organic values and the inorganic values of the typical groups are as shown in Tables 1 and 2 below.

TABLE 1

| Inorganic group | Inorganic Value |
|---|---|
| Light metal | 500< |
| Heavy metal, amine, and $NH_4$ group | 400< |
| —COOH | 150 |
| —OH | 100 |
| >CO | 65 |
| —COOφ | 60 |
| —O— | 20 |
| Benzene ring | 15 |
| Triple bond | 3 |
| Double bond | 2 |

TABLE 2

| Organic-Inorganic group | Inorganic Value | Organic Value |
|---|---|---|
| —Cl | 10 | 40 |
| >SO | 140 | 40 |
| —NO | 50 | 50 |
| Iso-branch | 0 | −10 |
| Tert.-branch | 0 | −20 |

Examples of the polar oil include ester oils such as diisobutyl adipate (0.46), 2-hexyldecyl adipate (0.25), di-2-heptylundecyl adipate (0.18), isocetyl isostearate (0.09), hexyl isostearate (0.13), trimethylolpropane triisostearate (0.58), ethylene glycol di-2-ethylhexanoate (0.35), cetyl 2-ethylhexanoate (0.13), trimethylolpropane tri-2-ethylhexanoate (0.35), pentaerythritol tetra-2-ethylhexanoate (0.38), cetyl octanoate (0.13), oleyl oleate (0.09), octyldodecyl oleate (0.08), isodecyl oleate (0.11), decyl oleate (0.11), neopentyl glycol dioctanoate (0.32), neopentyl glycol dicaprirate (0.25), triethyl citrate (0.86), dioctyl succinate (0.32), amyl acetate (0.50), ethyl acetate (0.75), butyl acetate (0.50), isocetyl stearate (0.09), butyl stearate (0.14), diisopropyl sebacinate (0.40), di-2-ethylhexyl sebacinate (0.24), cetyl lactate (0.42), myristyl lactate (0.47), isononyl isononanate (0.20), isotridecyl isononanate (0.16), isopropyl palmitate (0.16), 2-ethylhexyl palmitate (0.13), 2-hexyldecyl palmitate (0.95), cholesteryl 12-hydroxystearate (0.39), isopropyl myristate (0.18), octyldodecyl myristate (0.09), isocetyl myristate (0.10), decyl myristate (0.13), myristyl myristate (0.11), hexyldecyl dimethyloctanoate (0.18), ethyl laurate (0.21), hexyl laurate (0.17), 2-octyldodecyl N-lauroyl-L-glutamate (0.43), lauroylsarcosine isopropyl ester (0.96), and diisostearyl malate (0.28); and glyceride oils such as glycerol triisooctanoate (0.35), glyceryl triisostearate (0.16), glyceryl triisopalmitate (0.18), glyceryl tribehenate (0.14), glyceryl monostearate (0.62), glyceryl di-2-heptylundecanoate (0.29), glyceryl trimyristate (0.20) and diglyceryl myristyl isostearate (0.45). The numerals in parentheses are the IOB values of the oils.

The present component (B) may comprise a silicone oil. The IOB of silicone oils is approximately 0.15 to 0.40. Silicone oils may be added in addition to the aforementioned polar oil having the IOB of 0.05 to 1.0. Even when the oil is a mixture of the silicone oil and the polar oil, the present invention provides a cosmetic film which has good adhesion, is uniform, has no color unevenness and good coloring, on account of the powder surface-treated with the compound represented by the formula (1).

Examples of the silicone oils include linear or branched organopolysiloxane having a low viscosity to a high viscosity, such as dimethylpolysiloxane, tristrimethylsiloxymethylsilane, caprylyl methicone, phenyl trimethicone, tetrakistrimethylsiloxysilane, methylphenylpolysiloxane, methylhexylpolysiloxane, methylhydrogenpolysiloxane, and dimethylsiloxane-methylphenylsiloxane-copolymer; cyclic organopolysiloxanes such as octamethylcyclotetrasiloxane, decamethylcyclopentasiloxane, dodecamethylcyclohexasiloxane, tetramethyltetrahydrogencyclotetrasiloxane, and tetramethyltetraphenylcyclotetrasiloxane; silicone rubbers such as amino-modified organopolysiloxane, pyrrolidone-modified organopolysiloxane, pyrrolidone carboxylic acid-modified organopolysiloxane, dimethylpolysiloxane rubber having a high polymerization degree, amino-modified organopolysiloxane rubber, and dimethylsiloxane-methylphenylsiloxane-copolymer rubber; a cyclic organopolysiloxane solvent containing a silicone rubber or elastomer, trimethylsiloxysilicate, a cyclic siloxane solvent containing trimethylsiloxysilicate, higher alkoxy-modified silicones such stearoxy silicones, higher fatty acid-modified silicones; alkyl-modified silicones; long-chain alkyl-modified silicones; amino-modified silicones, fluorized silicone, silicone resins and a melt of a silicone resin.

A content of the silicone oil may be properly selected depending on a form of the cosmetic. In particular, the amount is 1 to 70 weight %, further preferably 1 to 50 weight %, based on a total weight of the cosmetic. When the oil is a mixture of the silicone oil and the polar oil, the amount of the silicon oil is properly controlled so that a total amount of the oils is 1 to 70 weight %, preferably 1 to 50 weight %, based on a total weight of the cosmetic.

Further, hydrocarbon oils, higher alcohols and fluorinated oils may be used, besides the polar oil and the silicone oil mentioned above.

Examples of the hydrocarbon oils include linear or branched hydrocarbon oil which may be volatile, such as ozokerite, α-olefin oligomers, light isoparaffin, isododecane, isohexadecane, light liquid isoparaffin, squalane, sysnthetic squalane, plant squalane, squalene, ceresin, paraffin, paraffin wax, polyethylene wax, polyethylene-polypropylene wax, (ethylene/propylene/styrene) copolymer, (butylenes/propylene/styrene) copolymer, liquid paraffin, liquid isoparaffin, pristane, polyisobutylene, hydrogenerated polyisobutylene, microcrystalline wax, and vaseline.

Examples of the higher alcohols include lauryl alcohol, myristyl alcohol, palmityl alcohol, stearyl alcohol, behenyl alcohol, hexadecyl alcohol, oleyl alcohol, isostearyl alcohol, hexyldodecanol, octyl dodecanol, cetostearyl alcohol, 2-decyltetradecinol, cholesterol, phytosterol, POE cholesterol ether, monostearyl glycerin ether (batyl alcohol), and monooleyl glyceryl ether (or cerakyl alcohol).

Examples of the fluorinated oil include perfluoropolyethers, perfluorodecaline and perfluorooctane.

Examples of the other oil include natural ester oils such as avocado oil, linseed oil, almond oil, Ibota wax, insect wax, perilla oil, olive oil, cacao butter, kapok wax, kaya oil, carnauba wax, liver oil, candelilla wax, purified candelilla wax, beef tallow, neat's-foot oil, beef bone fat, hydrogenated beef tallow, apricot kernel oil, spermaceti wax, hydrogenated oil, wheat germ oil, sesame oil, rice germ oil, rice bran oil, sugar cane wax, sasanqua oil, safflower oil, shear butter, Chinese tung oil, cinnamon oil, jojoba wax, squalane, squalene, shellac wax, turtle oil, soybean oil, tea seed oil, camellia oil, evening primrose oil, corn oil, lard, rapeseed oil, Japanese tung oil, rice bran oil, germ oil, horse fat, persic oil, palm oil, palm kernel oil, castor oil, hydrogenated castor oil, castor oil fatty acid methylester, sunflower oil, grape oil, bayberry wax, jojoba oil, macadamia nut oil, beeswax, mink oil, meadowfoam oil, cottonseed oil, cotton wax, Japanese wax, Japanese wax kernel oil, montan wax, coconut oil, hydrogenated coconut oil, tri-coconut oil fatty acid glyceride, mutton tallow, peanut oil, lanolin, liquid lanolin, hydrogenated lanolin, lanolin alcohol, hard lanolin, lanolin acetate, lanolin alcohol acetate, lanolin fatty acid isopropyl ester, POE lanolin alcohol ether, POE lanolin alcohol acetate, polyethylene glycol lanolin fatty acid, POE hydrogenated lanolin alcohol ether, and egg yolk oil.

The present cosmetic may contain ultraviolet light absorbents if needed. Examples of the ultraviolet light absorbents include those of benzoic acid type, such as p-aminobenzoic acid, ethyl p-aminobenzoate, glyceryl p-aminobenzoate and p-dimethylaminooctyl bezoate; those of anthranilic acid type, such as methyl anthranilate; those of salicylic acid type such as methyl salicylate, octyl salicylate, trimethylcyclohexyl salicylate, ethylene glycol salicylate and phenyl salicylate; those of cinnamic acid type such as benzyl cinnamate, octyl p-methoxy cinnamate and 2-ethoxyethyl-p-methoxy cinnamate; those of benzophenone type such as 2,4-dihydroxy benzophenone, tetrahydroxy benzophenone and hydroxymethoxy benzophenone; those of urocanic acid type such as urocanic acid and ethyl urocanate; those of dibenzoyl methane type such as 4-isopropyl-dibenzoyl methane and 4-tert-butyl-4'-methoxy-dibenzoyl methane; phenylbenzimidazole sulfonic acid; and triazine derivatives.

The present cosmetic may contain one or more silicone surfactants represented by the following general formula (3), depending on intended application.

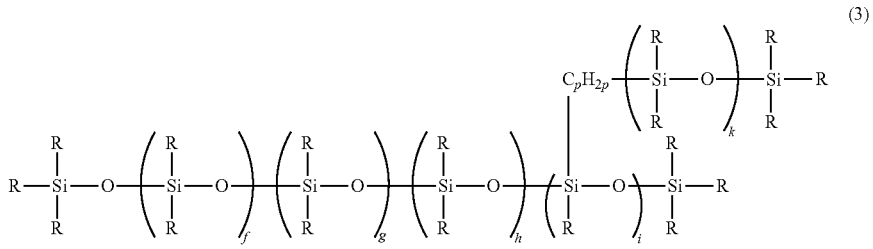

wherein R is, independently of each other, a substituted or unsubstituted, monovalent hydrocarbon group having 1 to 30 carbon atoms, and $R^7$ is, independently of each other, represented by the following formula (4) or (5). The unit derived from ethylene oxide or propylene oxide in the following formula (4) may form a block or bond randomly. The unit derived from glycerin in the following formula (5) may have a branched structure to constitute an isomer, $$—C_pH_{2p}O(C_2H_4O)_q(C_3H_6O)_mR^9 \qquad (4)$$

$$—C_pH_{2p}O(C_3H_5(OR^{10})O)_nR^{11} \qquad (5)$$

wherein $R^8$ is a monovalent hydrocarbon group having 6 to 30 carbon atoms, $R^9$, $R^{10}$ and $R^{11}$ are, independently of each other, a hydrogen atom or a monovalent hydrocarbon group having 1 to 6 carbon atoms, and at least one of $R^{10}$ and $R^{11}$ is a hydrogen atom. f is an integer of from 0 to 200, g is an integer of from 1 to 30, h is an integer of from 0 to 50, i is an integer of from 0 to 30, p is an integer of from 1 to 6, k is an integer of from 0 to 100, q is an integer of from 0 to 50, m is an integer of from 0 to 50, provided that a total of q and m is 1 or more, and n is an integer of from 1 to 6.

The compound having the group represented by the formula (4) is a silicone surfactant having a moiety derived from ethylene oxide and/or a moiety derived from propylene oxide as a hydrophilic moiety. The compound having the group represented by the formula (5) is a silicone surfactant having a moiety derived from glycerin as a hydrophilic moiety. These surfactants function as an emulsifier and have a good moisture-holding property. The emulsion with these fits easily to a skin and gives a very soft and moist feel.

In the formula (3), R is, independently of each other, a substituted or unsubstituted, monovalent hydrocarbon group having 1 to 30 carbon atoms, preferably an alkyl group having 1 to 30 carbon atoms, a halogen-substituted alkyl group having 1 to 15 carbon atoms, or an aryl group having 6 to 12 carbon atoms. Examples of R includes an alkyl group such as methyl, ethyl, propyl, butyl, pentyl, hexyl, heptyl, octyl, nonyl, decyl and stearyl groups; a cycloalkyl group such as cyclopentyl and cyclohexyl groups; an aryl group such as phenyl, ethyl phenyl and propylphenyl groups; and those groups where a part or the whole of their hydrogen atoms is (are) replaced with a halogen atom (s), such as fluorine, chlorine, bromine, and iodine atoms. The fluorine-substituted groups include fluorine-substituted alkyl groups such as a trifluoropropyl group and a heptadecafluoro decyl group. Among these, an alkyl group having 1 to 15 carbon atoms and a phenyl group are preferred.

In the aforesaid formulas (4) and (5), $R^9$, $R^{10}$ and $R^{11}$ are a hydrogen atom or a hydrocarbon group having 1 to 6 carbon atoms. Examples of the hydrocarbon group include methyl, ethyl, propyl, butyl, pentyl and hexyl groups. Preferred are a hydrogen atom, a methyl group and a butyl group. At least one of $R^{10}$ and $R^{11}$ is a hydrogen atom.

f is 0 to 200, preferably 0 to 100, g is 1 to 30, preferably 1 to 20, h is 0 to 50, preferably 0 to 20, i is 0 to 30, preferably 0 to 10, p is 1 to 6, preferably 2 to 4, k is 0 to 100, preferably 0 to 50, q is 0 to 50, preferably 0 to 30, m is 0 to 50, preferably 0 to 30, provided that a total of q and m is 1 or more, and n is 1 to 6, preferably 1 to 4.

Examples of the compound having the group represented by the formula (4) include KF-6011, KF-6011P, KF-6012, KF-6013, KF-6015, KF-6017, KF-6017P, KF-6028, KF-6028P, KF-6038 and KF-6043, all from Shin-Etsu Chemical Co., Ltd. Examples of the compound having the group represented by the formula (5) include KF-6100, KF-6104 and KF-6105, all from Shin-Etsu Chemical Co., Ltd.

An amount of the compound represented by the formula (3) may properly be selected depending on a form of the cosmetic. In particular, the amount is preferably 1 to 50 weight %, based on a total weight of the cosmetic.

The present cosmetic may contain one or more acryl, silicone-graft copolymers, depending on the intended use. Examples of the acryl, silicone-graft copolymers include KP-541, KP-543, KP-545, KP-549, KP-550, KP-545L, KP-561P, KP-562P, KP-575 and KP-578, all from Shin-Etsu Chemical Co., Ltd.

An amount of the acryl, silicone-graft copolymer may be properly selected depending on a form of the cosmetic. In particular, the amount is preferably 0.1 to 30 weight %, based on a total weight of the cosmetic.

The present cosmetic may contain one or more compounds having an alcoholic hydroxyl group, depending on the intended use. Examples of the compound having an alcoholic hydroxyl group which can be added in the present cosmetic include lower monohydric alcohols such as ethanol and isopropanol; sugar alcohols such as sorbitol and maltose; sterols such as cholesterol, sitosterol, phytosterol and lanosterol; and polyhydric alcohols such as butylene glycol, propylene glycol, dibutylene glylcol and pentylene glycol.

The present cosmetic may contain one or more water-soluble or water-swellable polymers. Examples of the polymer include plant polymers such as gum arabic, tragacanth gum, galactan, carob gum, guar gum, karaya gum, carrageenan, pectin, agar, quince seed (i.e., marmelo), starch from rice, corn, potato or wheat, algae colloid, trant gum and locust bean gum; bacteria-derived polymers such as xanthan gum, dextran, succinoglucan, and pullulan; animal-derived polymers such as collagen, casein, albumin, and gelatin; starch-derived polymers such as carboxymethyl starch and methylhydroxypropyl starch; cellulose polymers such as methyl cellulose, ethyl cellulose, methylhydroxypropyl cellulose, carboxymethyl cellulose, hydroxymethyl cellulose, hydroxypropyl cellulose, nitrocellulose, sodium cellulose sulfate, sodium carboxymethyl cellulose, crystalline cellulose, and cellulose powder; alginic acid-derived polymers such as sodium alginate and propylene glycol alginate; vinyl polymers such as polyvinyl methylether and carboxyvinyl polymer; polyoxyethylene polymers, polyoxyethylene/polyoxypropylene copolymers; acrylic polymers such as sodium polyacrylate, polyethyl acrylate, polyacrylamide and acryloyldimethyl taurate copolymer; water-soluble synthetic polymer such as polyethyleneimine and cationic polymers; and water-soluble inorganic polymers such as bentonite, aluminum magnesium silicate, montmorillonite, videlite, nontronite, saponite, hectorite and silicic anhydride. Film-forming agents, such as polyvinyl alcohol and polyvinyl pyrrolidone, are also included.

The present cosmetic may contain one or more surfactants, depending on the intended use. Any surfactants usually used in cosmetics can be used. For instance, anionic, cationic, nonionic or amphoteric surfactants can be used.

Examples of the anionic surfactants include fatty acid soaps such as sodium stearate and triethanolamine palmitate; alkylether carboxylic acids and salts thereof; salts of condensates of amino acids with fatty acids; alkanesulfonates, alkenesulfonates, sulfonates of fatty acid esters, fatty acid amide sulfonates, sulfonates of formalin condensates, alkylsulfates, sulfates of secondary higher alcohols, alkyl/allyl ether sulfates, sulfates of fatty acid esters, sulfates of fatty acid alkylolamides, and sulfates of Turkey Red oil; and alkyl phosphates, ether phosphates, alkylallylether phosphates, amide phosphates, N-acyl lactate, N-acyl sarcosinate and N-acylamino acid activates.

Examples of the cationic surfactants include alkylamine salts, amine salts of polyamine and amino alcohol fatty acid derivatives, alkyl quaternary ammonium salts, aromatic quaternary ammonium salts, pyridinium salts and imidazolium salts.

Examples of the nonionic surfactants include sorbitan fatty acid esters, glycerin fatty acid esters, polyglycerin fatty acid esters, propylene glycol fatty acid esters, polyethylene glycol fatty acid esters, sucrose fatty acid esters, methylglucoside fatty acid esters, alkylpolyglucoside, polyoxyethylene alkylethers, polyoxypropylene alkylethers, polyoxyethylene alkylphenylethers, polyoxyethylene fatty acid esters, polyoxyethylene sorbitan fatty acid esters, polyoxyethylene sorbitol fatty acid esters, polyoxyethylene glycerin fatty acid esters, polyoxyethylene propylene glycol fatty acid esters, polyoxyethylene castor oil, polyoxyethylene hydrogenated castor oil, polyoxyethylene phytostanolether, polyoxyethylene phytosterolether, polyoxyethylene cholestanolether, polyoxyethylene cholesterylether, linear or branched polyoxyalkylene-modifed organopolysiloxane, linear or branched polyoxyalkylene/alkyl co-modified-organopolysiloxane, linear or branched polyglycerin-modified organopolysiloxane, linear or branched polyglycerin/alkyl co-modified-organopolysiloxane, alkanolamide, sugar ethers, and sugar amides.

Examples of the amphoteric surfactants include betaine, phosphatidylcholine, aminocarboxylates, imidazoline derivatives and amide or amine type surfactants.

The present cosmetic may contain one or more silicone resins, depending on the intended use. The silicone resin is preferably a compound having a three-dimensional cross-linked structure, such as a silicone resin consisted of $R^1_3SiO_{0.5}$ units and $SiO_2$ units, a silicone resin consisted of $R^1_3SiO_{0.5}$ units, $R^1_2SiO$ units and $SiO_2$ units, a silicone resin consisted of $R^1_3SiO_{0.5}$ units and $R^1SiO_{1.5}$ units, a silicone resin consisted of $R^1_3SiO_{0.5}$ units, $R^1_2SiO$ units and $R^1SiO_{1.5}$ units, a silicone resin consisted of $R^1_3SiO_{0.5}$ units, $R^1_2SiO$ units, $R^1SiO_{1.5}$ units and $SiO_2$ units. The aforesaid $R^1$ are as defined above for $R^1$. Compounds having at least one structure selected from the group consisting of a pyrolidone structure, a long chain alkyl structure, a polyoxyalkylene structure, a flouroalkyl structure and an amino structure can be used.

Examples of the silicone resin include KF-7312J, KF-7312K, KF-7312T, X-21-5249, X-21-5250, KF-9021, X-21-5595 and X-21-5616, all from Shin-Etsu Chemical Co., Ltd.

The present cosmetic may contain one or more crosslinking organopolysiloxanes comprising oil which is liquid at room temperature, depending on the intended use. Preferably, the crosslinking organopolysiloxane is swelled with the liquid oil of a larger weight amount than that of the organopolysiloxane. Examples of the liquid oil include silicone oils, hydrocarbon oils, ester oils, natural oils from animals and plants, semi-synthetic oils and flouorinated oils; silicone oils having a low kinetic viscosity of from 0.65 mm$^2$/sec to 100.0 mm$^2$/sec at 25 degrees C.; hydrocarbon oils such as liquid paraffin, squalane, isododecane and isohexadecane; glyceride oils such as trioctanoin; esters such as isotridecyl isononanate, N-acyl glutamic acid ester and lauroylsarcosine ester; and natural oils from animals and plants, such as macadamia nut oil. The cross-linking organopolysiloxane may preferably form a cross-linked structure via an addition reaction between an alkenyl group and a hydrosilyl group, such as an organopolysiloxane having two or more vinyl groups in the molecular, a polyoxyalkylene having two or more allyl groups in the molecular, a polyglycerin having two or more allyl groups in the molecular, and α, ω-alkenyl diene. A cross-linking organopolysiloxane may have at least one selected from the group consisting of a polyoxyalkylene moiety, a polyglycerin moiety, a long chain alkyl moiety, an alkenyl moiety, an aryl moiety and a fluoroalkyl moiety.

Examples of the crosslinking organopolysiloxane include KSG-15, KSG-1510, KSG-16, KSG-1610, KSG-18A, KSG-41A, KSG-42A, KSG-43, KSG-44, KSG-045Z, KSG-210, KSG-310, KSG-320, KSG-330, KSG-340, KSG-320Z, KSG-350Z, KSG-360Z, KSG-710, KSG-810, KSG-820, KSG-840, KSG-840, KSG-820Z and KSG-850Z, all from Shin-Etsu Chemical Co., Ltd.

The present cosmetic may contain one or more kinds of silicone wax, depending on the intended use. The silicone wax is a silicone-modified olefin wax obtained by addition reaction between organohydrogenpolysiloxane having at least one SiH bond in a molecule and an olefin wax which was prepared from α-olefin and diene and still has an unsaturated group. The α-olefin preferably has 2 to 12 carbon atoms, such as ethylene, propylene, 1-butene, 1-hexene, and 4-methyl-1-pentene. The diene is preferably butadiene, isoprene, 1,4-hexadiene, vinyl norbornene, ethylidene norbornene, and dicyclopentadiene. The organohydrogenpolysiloxane having an SiH bond may have a linear or branched structure.

The cosmetic of the present invention may comprise other components that are commonly used in cosmetics in such an amount as not to adversely affect the present effect of the invention. Examples of the components include oil-soluble gelling agents, clay minerals modified with organic compounds, resins, antiperspirant, moisture retention agents, antiseptics, anti-microbial agents, perfumes, salts, antioxidants, pH regulators, chelating agents, refreshing agents, anti-inflammatory agents, skin-beautifying components such as skin whitener, cell activator, rough dry skin improver, blood circulation promoter, skin astringent and anti-seborrheic agent, vitamins, amino acids, nucleic acids, hormones, clathrate compounds and hair-setting agents.

Examples of the oil-soluble gelling agent include metal soaps, such as aluminum stearate, magnesium stearate and zinc myristate; amino acid derivatives, such as N-lauroyl-L-glutamic acid and α, γ-di-n-butylamine; dextrin fatty acid esters, such as dextrin palmitic acid ester, dextrin stearic acid ester and (palmitate/ethylhexanoate) dextrin; sucrose fatty acid esters, such as sucrose palmitic acid ester and sucrose stearic acid ester; fructooligosaccharide fatty acid esters, such as fructooligosaccharide stearate and fructooligosaccharide 2-ethylhexanoate; benzylidene derivatives of sorbitol, such as monobenzylidene sorbitol and dibenzylidene sorbitol; and clay minerals modified with organic compounds, such as dimethylbenzyldodecyl ammonium montmorillonite clay and dimethyldioctadecyl ammonium montmorillonite clay.

Examples of the antiperspirant include aluminum chlorohydrate, aluminum chloride, aluminum sesqui chlorohydrate, zirconyl hydroxychloride, aluminum zirconium hydroxychloride, and aluminum zirconium glycine complex.

Examples of the moisture retention agent include glycerin, sorbitol, propylene glycol, dipropylene glycol, 1,3-butylene glycol, pentylene glycol, glucose, xylitol, maltitol, polyethylene glycol, hyaluronic acid, chondroitin sulfuric acid, pyrrolidone carboxylate, polyoxyethylene glycoside, polyoxypropylene methylglycoside, egg yolk lecithin, soybean lecithin, phosphatidylcholine, phosphatidylethanolamine, phosphatidylserine, phosphatidylglycerol, phosphatidylinositol, and phosphosphingolipid.

Examples of the antiseptics include alkyl p-oxybenzoates, benzoic acid, sodium benzoate, sorbic acid, potassium sorbate, and phenoxyethanol. For the antibacterial agents, benzoic acid, salicylic acid, carbolic acid, sorbic acid, paraoxybenzoic acid alkyl esters, parachloromethacresol, hexachlorophene, benzalkonium chloride, chlorohexydine chloride, trichlorocarbanilide, photosensitizers and phenoxyethanol.

Examples of the salts include inorganic salts, organic acid salts, amine salts and amino acid salts. Examples of the inorganic salts include sodium salts, potassium salts, magnesium salts, calcium salts, aluminum salts, zirconium salts, or zinc salts of inorganic acids such as hydrochloric acid, sulfuric acid, carbonate, and nitric acid. Examples of the organic acid salts include a salt of an organic acid such as acetic acid, dehydro acetic acid, citric acid, malic acid, succinic acid, ascorbic acid and stearic acid. Examples of the amine salts and the amino acid salts include salts of amines such as triethanolamine and salts of amino acids such as glutamic acid. Further, hyaluronic acid, salts such as chondroitin sulfate, and aluminum zirconium glycine complex, and neutralized salt of an acid and an alkali which is usually used in cosmetic formulations can also be used.

Examples of the antioxidants include tocopherol, p-t-butylphenol, butylhydroxyanisole, dibutylhydroxytoluene and phytic acid. Examples of the pH regulators include lactic acid, citric acid, glycolic acid, succinic acid, tartaric acid, dl-malic acid, potassium carbonate, sodium hydrogen carbonate and ammonium hydrogen carbonate. Examples of the chelating agents include alanine, sodium edetate, sodium polyphosphate, sodium metaphosphate and phosphoric acid. Examples of the refreshing agents include L-menthol and camphor. Examples of the anti-inflammatory agents include allantoin, glycyrrhizinic acid and salts thereof, glycyrrhetinic acid and stearyl glycyrrhetinate, tranexamic acid and azulene.

Examples of the skin-beautifying components include whitening agents include placenta extract, arbutin, glutathione and Yukinoshita extract; cell activators, such as royal jelly, photosensitizers, cholesterol derivatives and calf blood extract; rough and dry skin improvers; blood circulation improvers, such as nonylic acid vanillyl amide, benzyl nicotinate, beta-butoxyethyl nicotinate, capsaicin, zingerone, cantharis tincture, ichtammol, caffeine, tannic acid, alpha-borneol, tocopheryl nicotinate, inositol hexanicotinate, cyclandelate, cinnarizine, tolazoline, acetyl choline, verapamil, cepharanthin and gamma-oryzanol; skin astringents, such as zinc oxide and tannic acid; and anti-seborrheic agents, such as sulfur and thianthol.

Examples of the vitamins include vitamin A, such as vitamin A oil, retinol, retinyl acetate and retinyl palmitate; vitamin B, including vitamin B2 such as riboflavin, riboflavin butyrate and flavin adenine nucleotide, vitamin B6 such as pyridoxine hydrochloride, pyridoxine dioctanoate and pyridoxine tripalmitate, vitamin B12 and its derivatives, and vitamin B15 and its derivatives; vitamin C, such as L-ascorbic acid, L-ascorbic acid dipalmitic ester, L-ascorbic acid-2-sodium sulfate and L-ascorbic acid dipotassium diphosphate ester; vitamin D, such as ergocalciferol and cholecarciferol; vitamin E, such as alpha-tocopherol, beta-tocopherol, gamma-tocopherol, dl-alpha-tocopheryl acetate, dl-alpha-tocopheryl nicotinate and dl-alpha-tocopheryl succinate; vitamin H; vitamin P; nicotinic acids, such as nicotinic acid, benzyl nicotinate and nicotinic acid amide; pantothenic acids, such as calcium pantothenate, D-pantothenyl alcohol, pantothenyl ethyl ether and acetylpantothenyl ethyl ether; and biotin.

Examples of the amino acids include glycine, valine, leucine, isoleucine, serine, threonine, phenylalanine, arginine, lysine, aspartic acid, glutamic acid, cystine, cysteine, methionine, and tryptophan. Examples of the nucleic acids include deoxyribonucleic acid. Examples of the hormones include estradiol and ethenyl estradiol.

Examples of the polymers for setting hair include amphoteric, anionic, cationic, or nonionic polymer compounds. For instance, polyvinyl pyrrolidone polymer compounds such as polyvinyl pyrrolidone and vinyl pyrrolidone/vinyl acetate copolymers; acidic vinyl ether polymer compounds such as methyl vinyl ether/maleic anhydride alkyl half ester copolymer; acidic polyvinyl acetate polymers such as vinyl acetate/crotonic acid copolymers; acidic acrylic polymer compounds such as (meth) acrylic acid/alkyl (meth) acrylate copolymers, and (meth) acrylic acid/alkyl (meth) acrylate/ alkyl acrylamide copolymer; amphoteric acrylic polymer compounds such as N-methacryloylethyl-N,N-dimethylammonium-α-N-methyl carboxybetaine/alkyl(meth)acrylate copolymer, and hydroxypropyl(meth)acrylate/butylaminoethylmethacrylate/acrylic acid octyl amide copolymers. Further, polymer compounds obtained from natural products, such as cellulose or its derivatives, keratin, and collagen or its derivatives can be suitably used.

The cosmetic of the present invention may be in any form and is not limited to particular one. For instance, the cosmetic may be of powder, oil, water-in-oil emulsion, oil-in-water emulsion, nonaqueous emulsion, and multi-emulsion such as W/O/W or O/W/O.

For instance, the cosmetic includes skincare cosmetics such as a lotion, a milky lotion, a cream, a cleansing, a pack, an oil liquid, a massage agent, a beauty essence, a beauty oil, a detergent, a deodorant, a hand cream, a lip balm, and a wrinkle concealler; makeup cosmetics such as a make-up foundation, a concealer, a face powder, a powder foundation, a liquid foundation, a cream foundation, an oily foundation, a blush, an eye shadow, a mascara, an eyeliner, an eyebrow, and a lipstick; hair cosmetics such as a shampoo, a rinse, a treatments, and a setting agent; antiperspirants; and UV protective cosmetics such as a sunscreen oil, a sunscreen milky lotion, and a sunscreen cream.

Further, the present cosmetic may be in various forms such as liquid, emulsion, cream, solid, paste, gel, powder, pressed, laminated, mousse, spray, stick, and pencil forms.

EXAMPLES

The present invention will be explained in detail with reference to the following Examples, but not limited to them. In the following, "%" means "% by weight", unless otherwise specified.

Synthesis Example 1

To a reactor were added 164 parts by weight of the organohydrogenpolysiloxane represented by the following average composition formula (6):

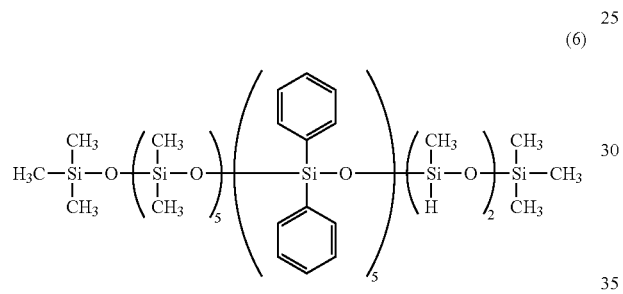

(6)

and 41.8 parts by weight of vinyltriethoxysilane, and further added 100 parts by weight of toluene. 0.1 Part of 0.5 wt % solution of chloroplatinic acid in toluene was added to the mixture, which was then allowed to react for 2 hours under reflux of the solvent. The reaction mixture was subsequently heated under a reduced pressure to distill off the solvent and the unreacted starting material to obtain 196 parts by weight of organopolysiloxane represented by the following average compositional formula (7).

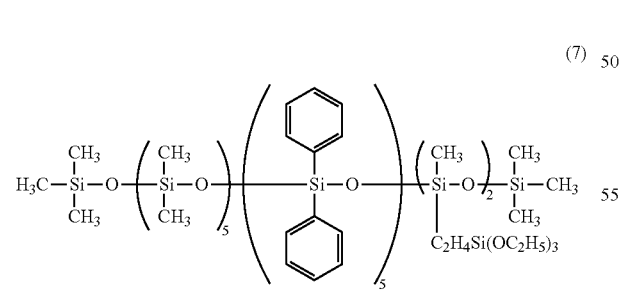

(7)

Synthesis Example 2

To a reactor were added 176 parts by weight of the organohydrogenpolysiloxane represented by the following average composition formula (8):

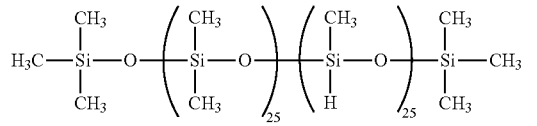

(8)

and 100 parts by weight of toluene. 0.15 Part of 0.5 wt % solution of a chloroplatinic acid in toluene was added to the mixture. The mixture was heated to 80 degrees C., to which 114 parts by weight of α-methylstyrene was added dropwise. Then, 31 parts by weight of vinyltriethoxysilane was added and the mixture was heated for 2 hours under reflux of the solvent and subsequently heated under a reduced pressure to distill off the solvent and the unreacted starting material to obtain 310 parts by weight of organopolysiloxane represented by the following average compositional formula (9).

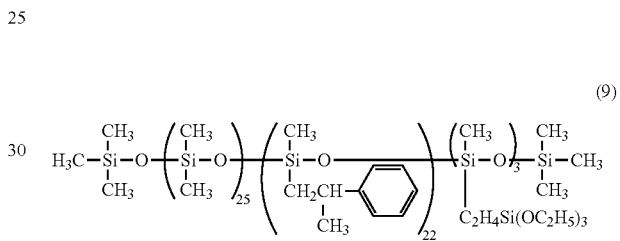

(9)

Synthesis Example 3

To a reactor were added 172 parts by weight of the organohydrogenpolysiloxane represented by the following average composition formula (10):

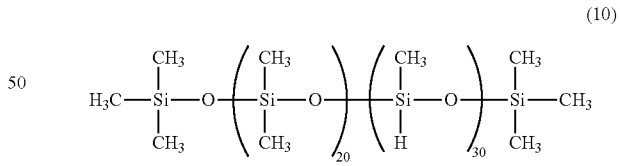

(10)

and 100 parts by weight of toluene. 0.15 Part of 0.5 wt % solution of a chloroplatinic acid in toluene was added to the mixture. The mixture was heated to 80 degrees C., to which 59 parts by weight of 1-dodecene and 104 parts by weight of α-methylstyrene were added dropwise. Then, 27 parts by weight of methylvinyldiethoxysilane was added and the mixture was heated for 2 hours under reflux of the solvent and subsequently heated under a reduced pressure to distill off the solvent and the unreacted starting material to obtain 355 parts by weight of organopolysiloxane represented by the following average compositional formula (11).

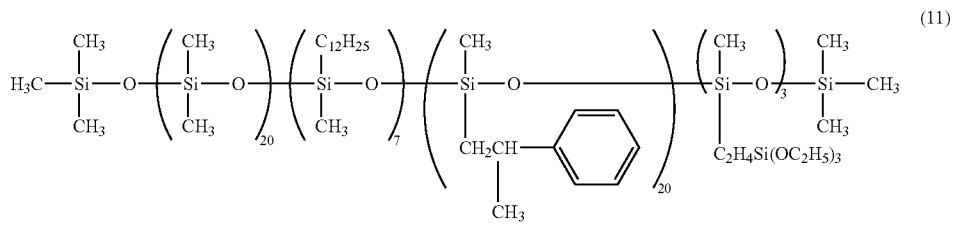
(11)

Comparative Synthesis Example 1

To a reactor were added 179 parts by weight of the organohydrogenpolysiloxane represented by the following average composition formula (12):

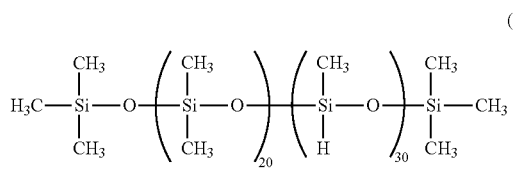
(12)

and 100 parts by weight of toluene. 0.1 Part of 0.5 wt % solution of a chloroplatinic acid in toluene was added to the mixture. The mixture was heated to 80 degrees C., to which 58 parts by weight of α-methylstyrene was added dropwise. Then, 50 parts by weight of vinyltriethoxysilane was added and the mixture was heated for 2 hours under reflux of the solvent and subsequently heated under a reduced pressure to distill off the solvent and the unreacted starting material to obtain 273 parts by weight of organopolysiloxane represented by the following average compositional formula (13).

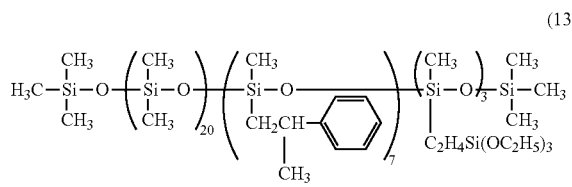
(13)

Comparative Synthesis Example 2

To a reactor were added 100 parts by weight of the organohydrogenpolysiloxane represented by the following average composition formula (14):

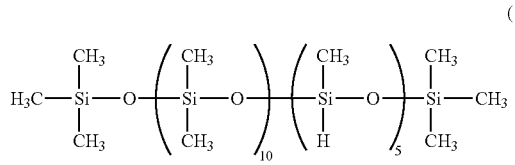
(14)

and 125 parts by weight of toluene. 0.3 Part of 0.5 wt % solution of a chloroplatinic acid in toluene was added to the mixture. Then, 248 parts by weight of an organopolysiloxane represented by the following general formula (15) was added dropwise to the mixture.

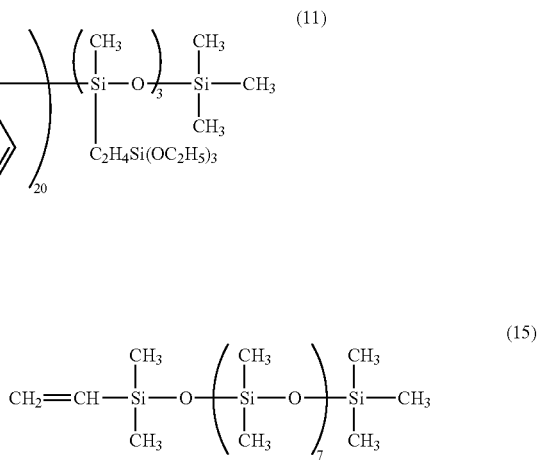
(15)

18.3 Parts by weight of vinyltriethoxysilane was further added dropwise, the mixture was heated for 6 hours under reflux of the solvent and subsequently heated under a reduced pressure to distill off the solvent to obtain 355 parts by weight of organopolysiloxane represented by the following average compositional formula (16).

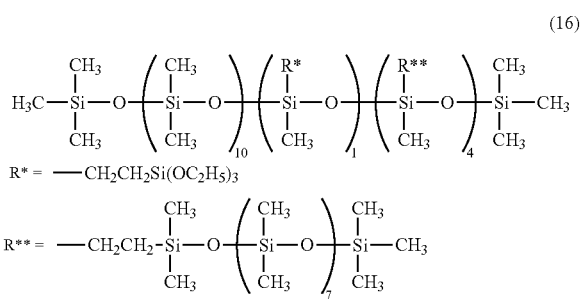
(16)

Preparation of Powder Surface-Treated with the Compound Obtained in the Aforesaid Synthesis Examples

[Treated Powder 1]

97 Parts of titanium oxide powder, TIPAQUE CR-50, ex Ishihara Sangyo Co., Ltd., 3 parts of the compound obtained in Synthesis Example 1, and 100 parts of toluene were added in a reactor, so that the powder was wet-treated. After distilling off the toluene under heating, the residue was heated for baking at 130 degrees C. for 3 hours to obtain Treated Powder 1.

[Treated Powder 2]

The process of the preparation of Treated Powder 1 was repeated to obtain Treated Powder 2, except that the compound obtained in Synthesis Example 2 was used in place of the compound obtained in Synthesis Example

[Treated Powder 3]

98 Parts of red iron oxide powder, R-516P, ex Titan Kogyo, Ltd., 2 parts of the compound obtained in Synthesis Example 1, and 100 parts of toluene were added in a reactor, so that the powder was wet-treated. After distilling off the toluene under heating, the residue was heated for baking at 130 degrees C. for 3 hours to obtain Treated Powder 3.

[Treated Powder 4]

The process of the preparation of Treated Powder 3 was repeated to obtain Treated Powder 4, except that the compound obtained in Synthesis Example 2 was used in place of the compound obtained in Synthesis Example

[Treated Powder 5]

98 Parts of yellow iron oxide powder, LL-100P, ex Titan Kogyo, Ltd., 2 parts of compound obtained in Synthesis Example 1, and 100 parts of toluene were added in a reactor, so that the powder was wet-treated. After distilling off the toluene under heating, the residue was heated for baking at 130 degrees C. for 3 hours to obtain Treated Powder 5.

[Treated Powder 6]

The process of the preparation of Treated Powder 5 was repeated to obtain Treated Powder 6, except that the compound obtained in Synthesis Example 2 was used in place of the compound obtained in Synthesis Example 1.

[Treated Powder 7]

98 Parts of black iron oxide powder, BL-100P, ex Titan Kogyo, Ltd., 2 parts of compound obtained in Synthesis Example 1, and 100 parts of toluene were added in a reactor, so that the powder was wet-treated. After distilling off the toluene under heating, the residue was heated for baking at 130 degrees C. for 3 hours to obtain Treated Powder 7.

[Treated Powder 8]

The process of the preparation of Treated Powder 7 was repeated to obtain Treated Powder 8, except that the compound obtained in Synthesis Example 2 was used in place of the compound obtained in Synthesis Example 1.

[Treated Powder 9]

95 Parts of ultrafine zinc oxide powder, MZ-500, ex Tayca Co., Ltd., 5 parts of compound obtained in Synthesis Example 1, and 200 parts of toluene were added in a reactor, so that the powder was wet-treated. After distilling off the toluene under heating, the residue was heated for baking at 130 degrees C. for 3 hours to obtain Treated Powder 5.

[Treated Powder 10]

98 Parts of talc powder, ex Nippon Talc Co., Ltd., 2 parts of compound obtained in Synthesis Example 1, and 100 parts of toluene were added in a reactor, so that the powder was wet-treated. After distilling off the toluene under heating, the residue was heated for baking at 130 degrees C. for 3 hours to obtain Treated Powder 10.

[Treated Powder 11]

98 Parts of sericite powder, ex Sanshin Koko Co., Ltd, 2 parts of compound obtained in Synthesis Example 2, and 100 parts of toluene were added in a reactor, so that the powder was wet-treated. After distilling off the toluene under heating, the residue was heated for baking at 130 degrees C. for 3 hours to obtain Treated Powder 11.

[Treated Powder 12]

The process of the preparation of Treated Powder 1 was repeated to obtain Treated Powder 12, except that the compound obtained in Comparative Synthesis Example 1 was used in place of the compound obtained in Synthesis Example 1.

[Treated Powder 13]

The process of the preparation of Treated Powder 3 was repeated to obtain Treated Powder 13, except that the compound obtained in Comparative Synthesis Example 1 was used in place of the compound obtained in Synthesis Example 1.

[Treated Powder 14]

The process of the preparation of Treated Powder 5 was repeated to obtain Treated Powder 14, except that the compound obtained in Comparative Synthesis Example 1 was used in place of the compound obtained in Synthesis Example 1.

[Treated Powder 15]

The process of the preparation of Treated Powder 7 was repeated to obtain Treated Powder 15, except that the compound obtained in Comparative Synthesis Example 1 was used in place of the compound obtained in Synthesis Example 1.

[Treated Powder 16]

The process of the preparation of Treated Powder 1 was repeated to obtain Treated Powder 16, except that the compound obtained in Comparative Synthesis Example 2 was used in place of the compound obtained in Synthesis Example 1.

[Treated Powder 17]

The process of the preparation of Treated Powder 3 was repeated to obtain Treated Powder 17, except that the compound obtained in Comparative Synthesis Example 2 was used in place of the compound obtained in Synthesis Example 1.

[Treated Powder 18]

The process of the preparation of Treated Powder 5 was repeated to obtain Treated Powder 18, except that the compound obtained in Comparative Synthesis Example 2 was used in place of the compound obtained in Synthesis Example 1.

[Treated Powder 19]

The process of the preparation of Treated Powder 7 was repeated to obtain Treated Powder 19, except that the compound obtained in Comparative Synthesis Example 2 was used in place of the compound obtained in Synthesis Example 1.

Examples 1 and 2, Comparative Example 1

The components shown in Table 3 were used to prepare W/O liquid foundations.

TABLE 3

| | Component | Content, part | | |
| --- | --- | --- | --- | --- |
| | | Example 1 | Example 2 | Comparative Example 1 |
| 1 | Cross-linked, polyether-modified silicons [Note 1)] | 3.5 | 3.5 | 3.5 |
| 2 | Cross-linked dimethylsilicone [Note 2)] | 5 | 5 | 5 |
| 3 | Branched-silicone type, polyether-modified silicone [Note 3)] | 2 | 2 | 2 |
| 4 | Dioctadecyldimethylammonium-modified montmorillonite | 1.2 | 1.2 | 1.2 |
| 5 | Glyceryl trioctanoate, IOB = 0.35 | 8 | 8 | 8 |
| 6 | Dimethylpolysiloxane, 6 mm$^2$/sec | 6.5 | 6.5 | 6.5 |
| 7 | Cyclopentasiloxane | 11.1 | 11.1 | 11.1 |
| 8 | Acryl-silicone graft copolymer [Note 4)] | 1.5 | 1.5 | 1.5 |

TABLE 3-continued

| | Content, part | | |
|---|---|---|---|
| Component | Example 1 | Example 2 | Comparative Example 1 |
| 9 Treated powder 1 | 8.5 | — | — |
| 10 Treated powder 3 | 0.97 | — | — |
| 11 Treated powder 5 | 0.41 | — | — |
| 12 Treated powder 7 | 0.12 | — | — |
| 13 Treated powder 2 | — | 8.5 | — |
| 14 Treated powder 4 | — | 0.97 | — |
| 15 Treated powder 6 | — | 0.41 | — |
| 16 Treated powder 8 | — | 0.12 | — |
| 17 Treated powder 12 | — | — | 8.5 |
| 18 Treated powder 13 | — | — | 0.97 |
| 19 Treated powder 14 | — | — | 0.41 |
| 20 Treated powder 15 | — | — | 0.12 |
| 21 Dispersion of fine particulate titanium oxide [Note 5] | 10 | 10 | 10 |
| 22 1,3-Butylene glycol | 5 | 5 | 5 |
| 23 Sodium citrate | 0.2 | 0.2 | 0.2 |
| 24 Water | 36 | 36 | 36 |

[1] Cross-linked, polyether-modified silicone: KSG-210, ex Shin-Etsu Chemical Co., Ltd.
[2] Cross-linked dimethyl silicone: KSG-15, ex Shin-Etsu Chemical Co., Ltd.
[3] Branched-silicone type, polyether-modified silicone: KF-6028, ex Shin-Etsu Chemical Co., Ltd.
[4] Acryl-silicone graft copolymer: KP-575, ex Shin-Etsu Chemical Co., Ltd.
[5] Dispersion of fine particle titanium oxide: SPD-T5, ex Shin-Etsu Chemical Co., Ltd.

Preparation Method

A: Components 1 to 5, a part of component 6 and a part of component 7 were mixed.

B: The rest of component 6, the rest of component 7, component 8 and the treated powder were mixed and ground with rolls.

C: Components 22 to 24 were dissolved together uniformly.

D: The mixture obtained in the step C was added to the mixture obtained in the step A with stirring.

E: The mixture obtained in the step B was added to the mixture obtained in the step D with stirring.

F: Component 21 was added to the mixture obtained in the step E with stirring.

Evaluations of Feeling in Use, Durability of a Makeup, Uniformity of a Film and Adhesion The W/O liquid foundations obtained above were used by 50 female expert panelists, and the feeling in use, adhesion, uniformity of a film and durability of a makeup were evaluated according to the following criteria.

5 points: good
4 points: slightly good
3 points: ordinary
2 points: slightly bad
1 point: bad The points were averaged and given the following grades. The results are shown in Table 4.

A: Average point was 4.5 or more
B: Average point was 3.5 or more to less than 4.5
C: Average point was 2.5 or more to less than 3.5
D: Average point was 1.5 or more to less than 2.5
E: Average point was less than 1.5

Storage Stability

The W/O liquid foundation obtained above was stored at 50 degrees C. for 1 week and, then, the appearance was visually observed to evaluate the storage stability. The results are shown in Table 4.

TABLE 4

| | Example 1 | Example 2 | Comparative Example 1 |
|---|---|---|---|
| Feeling in use | B | B | C |
| Adhesion | A | A | B |
| Uniformity of a film | A | A | C |
| Durability of makeup | A | A | C |
| Storage stability, after storage at 50 degrees C. for one week | No change | No change | Separation occurred and part of the powder precipitated. |

As shown in Table 4, the foundations obtained in Examples 1 and 2 had better feeling in use and adhesion, gave a uniform film without irregular color, and better durability of makeup, compared to the foundation obtained in Comparative Example 1. Further, after the storage at 50 degrees C. for one week, the foundation of Comparative Example 1 caused separation, but the foundations of Examples 1 and 2 were stable with no separation.

Examples 3 and 4, and Comparative Examples 2 and 3

The components shown in Table 5 were used to prepare W/O cream foundations.

TABLE 5

| Component | Example 3 | Example 4 | Comparative Example 2 | Comparative Example 3 |
|---|---|---|---|---|
| 1 Branched silicone/alkyl, cross-linked, polyether-modified silicon [Note 6] | 5 | 5 | 5 | 5 |
| 2 Branched silicone/alkyl, cross-linked dimethylsilicone [Note 7] | 5 | 5 | 5 | 5 |
| 3 Branched silicone/alkyl, polyether-modified silicone [Note 8] | 2 | 2 | 2 | 2 |
| 4 Dioctadecyldimethylammonium-modified montmorillonite | 1.5 | 1.5 | 1.5 | 1.5 |
| 5 Isotridecyl isononanate, IOB = 0.16 | 5 | 5 | 5 | 5 |
| 6 Octyl p-methoxy cinnamate, IOB = 0.28 | 5 | 5 | 5 | 5 |
| 7 Cyclopentasiloxane | 21 | 21 | 21 | 21 |
| 8 Branched silicone/alkyl, polyether-modified silicone [Note 8] | 0.5 | 0.5 | 0.5 | 0.5 |
| 9 Treated powder 1 | 8.5 | — | — | — |
| 10 Treated powder 3 | 0.97 | — | — | — |
| 11 Treated powder 5 | 0.41 | — | — | — |
| 12 Treated powder 7 | 0.12 | — | — | — |
| 13 Treated powder 2 | — | 8.5 | — | — |
| 14 Treated powder 4 | — | 0.97 | — | — |
| 15 Treated powder 6 | — | 0.41 | — | — |
| 16 Treated powder 8 | — | 0.12 | — | — |
| 17 Treated powder 12 | — | — | 8.5 | — |
| 18 Treated powder 13 | — | — | 0.97 | — |
| 19 Treated powder 14 | — | — | 0.41 | — |
| 20 Treated powder 15 | — | — | 0.12 | — |
| 21 Treated powder 16 | — | — | — | 8.5 |
| 22 Treated powder 17 | — | — | — | 0.97 |
| 23 Treated powder 18 | — | — | — | 0.41 |
| 24 Treated powder 19 | — | — | — | 0.12 |
| 25 1,3-Butylene glycol | 5 | 5 | 5 | 5 |
| 26 Sodium citrate | 0.2 | 0.2 | 0.2 | 0.2 |
| 27 Water | 36 | 36 | 36 | 36 |

[6] Branched silicone/alkyl, cross-linked, polyether-modified silicone: KSG-350Z, ex Shin-Etsu Chemical Co., Ltd.
[7] Branched silicone/alkyl, cross-linked dimethylsilicone: KSG-045Z, ex Shin-Etsu Chemical Co., Ltd.
[8] Branched silicone/alkyl, polyether-modified silicone: KF-6038, ex Shin-Etsu Chemical Co., Ltd.

Preparation Method
A: Components 1 to 6, and a part of component 7 were mixed.
B: Component 8, the treated powder and the rest of component 7 were mixed and ground with rolls.
C: Components 25 to 27 were dissolved together uniformly.
D: The mixture obtained in the step C was added to the mixture obtained in the step A with stirring.
E: The mixture obtained in the step B was added to the mixture obtained in the step D with stirring.

The obtained W/O cream foundations were evaluated in the same manner as in Example 1. The results are shown in Table 6.

TABLE 6

| | Example 3 | Example 4 | Comparative Example 2 | Comparative Example 3 |
|---|---|---|---|---|
| Feeling in use | A | A | C | B |
| Adhesion | B | A | B | B |
| Uniformity of a film | A | A | D | D |
| Durability of makeup | A | A | D | C |
| Storage stability, after storage at 50 degrees C. for one week | No change | No change | Separation occurred and part of the powder precipitated. | Separation occurred and part of the powder precipitated. |

As shown in Table 6, the foundations obtained in Examples 3 and 4 had better feeling in use and adhesion, gave a uniform film without irregular color, and better durability of makeup, compared to the foundations obtained in Comparative Examples 2 and 3. Further, after the storage at 50 degrees C. for one week, the foundations of Comparative Examples 2 and 3 caused separation, but the foundations of Examples 3 and 4 were stable with no separation.

Example 5: Powder Foundation

| Component | Weight(%) |
|---|---|
| 1. Treated powder 10 | 35.0 |
| 2. Treated powder 11 | 35.0 |
| 3. Treated powder 1 | 12.0 |
| 4. Treated powder 3 | 0.7 |
| 5. Treated powder 5 | 2.0 |
| 6. Treated powder 7 | 0.1 |
| 7. Spherical nylon powder, 5 μm | 5.0 |
| 8. Dimethylpolysiloxane, 6 mm$^2$/sec | 7.0 |
| 9. Glyceryl trioctanoate, IOB = 0.35 | 1.5 |
| 10. Dipentaerythritol fatty acid ester | 1.5 |
| 11. Antiseptic | 0.1 |
| 12. Perfume | 0.1 |

Preparation Method
A: Components 1 to 7 were added in a Henschel mixer and mixed with stirring.

B: Components 8 to 11 were dissolved together uniformly.
C: The mixture obtained in the step B and component 12 were added to the mixture obtained in the step A, which was then put in a container and pressed to obtain a powder foundation.

The powder foundation comprising the treated powders of the present invention spread lightly on the skin and did not have a powdery feel, was not sticky or oily, had good adhesion to the skin and gave a dry feeling in use.

In addition, water resistance, water repellency and perspiration resistance were good and durability of makeup was also good, and did not run. Further, the properties of the powder foundation did not change with time or upon change of the temperature to give excellent stability.

Example 6: Water-In-Oil Sunscreen Agent

| (Component) | Weight (%) |
| --- | --- |
| 1. Cyclopentasiloxane | 8.8 |
| 2. Dimethylpolysiloxane, 6 mm$^2$/sec | 8.0 |
| 3. Branched-silicone, polyether-modified silicone(Note 1) | 2.0 |
| 4. Octyl p-methoxy cinnamate, IOB = 0.28 | 7.5 |
| 5. Dioctadecyldimethylammonium-modified montmorillonite | 0.2 |
| 6. Hybrid silicone composite powder(Note 2) | 0.5 |
| 7. Treated powder 9/Cyclopentasiloxane dispersion(Note 3) | 44.0 |
| 8. Sodium citrate | 0.7 |
| 9. 1,3-Butylene glycol | 3.0 |
| 10. Ethanol | 5.0 |
| 11. Perfume | 0.1 |
| 12. Purified water | 20.2 |

(Note 1)
Branched-silicone type, polyether-modified silicone: KF-6028, ex Shin-Etsu Chemical Co., Ltd.
(Note 2)
Hybrid silicone composite powder: KSP-105, ex Shin-Etsu Chemical Co., Ltd.
(Note 3)
Treated powder 9/Cyclopentasiloxane dispersion: Dispersion prepared by mixing 60 parts of treated powder 9, 35 parts of cyclopentasiloxane, and 5 parts of acryl-silicone graft copolymer, KP-578, ex Shin-Etsu Chemical Co., Ltd., and treating with a beads mill.

Preparation Method
A: Components 1 to 6 were mixed.
B: Components 8 to 10 and 12 were mixed to dissolve together.
C: The mixture obtained in the step B was added to the mixture obtained in the step A and emulsified and, then component 7 was added to the emulsion and stirred.
D: Component 11 was added to the mixture obtained in the step C to obtain a sunscreen agent.

The sunscreen agent comprising the present treated powder had no stickiness and an excellent adhesion, and gave a uniform film, and an excellent durability of makeup.

Example 7: Oil-In-Water Cream

| (Component) | Weight(%) |
| --- | --- |
| 1. Ethanol | 15.0 |
| 2. Propylene glycol | 3.0 |
| 3. Polyether-modified silicone(Note 1) | 0.5 |
| 4. Glyceryl trioctanoate, IOB = 0.35 | 2.0 |
| 5. Dimethylpolysiloxane, 6 mm$^2$/sec | 2.0 |
| 6. Treated powder 11 | 3.0 |
| 7. Hybrid silicone composite powder(Note 2) | 5.0 |
| 8. Carboxyvinyl polymer, aqueous 1% solution | 20.0 |
| 9. Xanthan gum, aqueous 2% solution | 6.0 |
| 10. Triethanolamine | 0.2 |
| 11. Antiseptic | 0.1 |
| 12. Perfume | 0.1 |
| 13. Purified water | 60.6 |

(Note 1)
Polyether-modified silicone: KF-6011, ex Shin-Etsu Chemical Co., Ltd.
(Note 2)
Hybrid silicone composite powder: KSP-100, ex Shin-Etsu Chemical Co., Ltd.

Preparation Method
A: Components 1 to 7 were mixed.
B: Components 8 to 13 were mixed to dissolve together.
C: The mixture obtained in the step A was added to the mixture obtained in the step B, stirred to emulsify.

The oil-in-water cream comprising the present treated powder had no stickiness or oiliness, gave moist, fresh, and refreshing feeling. In addition, the durability of makeup was excellent and the makeup did not change with time or in temperature change and, therefore, the stability was excellent.

Example 8: Body Lotion

| (Component) | Weight (%) |
| --- | --- |
| 1. Ethanol | 14.0 |
| 2. Cyclopentasiloxane | 3.0 |
| 3. 1,3-Butylene glycol | 3.0 |
| 4. Branched-silicone, polyglycerin-modified silicone(Note 1) | 0.5 |
| 5. Glyceryl trioctanoate, IOB = 0.35 | 2.0 |
| 6. Treated powder 10 | 5.0 |
| 7. Hybrid silicone composite powder(Note 2) | 5.0 |
| 8. Ammonium acryloyl dimethyltaurate/VP copolymer, aqueous 2% solution | 20.0 |
| 9. Xanthan gum, aqueous 2% solution | 6.0 |
| 10. Sodium chloride, aqueous 1% solution | 1.0 |
| 11. Antiseptic | 0.1 |
| 12. Perfume | 0.1 |
| 13. Purified water | 40.3 |

(Note 1)
Branched-silicone type, polyglycerin-modified silicone: KF-6100, ex Shin-Etsu Chemical Co., Ltd.
(Note 2)
Hybrid silicone composite powder: KSP-100, ex Shin-Etsu Chemical Co., Ltd.

Preparation Method
A: Components 1 to 7 were mixed.
B: Components 8 to 13 were mixed to dissolve together.
C: The mixture obtained in the step A was added to the mixture obtained in the step B and mixed with stirring to obtain a body lotion.

The body lotion comprising the present treated powder had no stickiness or oiliness, gave moist, fresh, and refreshing feeling. In addition, the makeup did not change with time or in temperature change and, therefore, the stability was excellent.

Example 9: Water-In-Oil Cream

| (Component) | Weight (%) |
| --- | --- |
| 1. Dimethylpolysiloxane, 6 mm$^2$/sec | 6.0 |
| 2. Methylphenyl polysiloxane | 4.0 |
| 3. Squalane | 5.0 |

-continued

| (Component) | Weight (%) |
|---|---|
| 4. Neopentyl glycol dioctanoate, IOB = 0.32 | 3.0 |
| 5. Polyether-modified silicone(Note 1) | 3.0 |
| 6. Hydrophobized titanium oxide fine powder(Note 2) | 2.0 |
| 7. Magnesium sulfate | 0.7 |
| 8. Glycerin | 10.0 |
| 9. Antiseptic | 0.1 |
| 10. Perfume | 0.1 |
| 11. Purified water | 66.1 |

(Note 1)
Polyether-modified silicone: KF-6017, ex Shin-Etsu Chemical Co.
(Note 2)
Hydrophobized titanium oxide fine powder: Titanium oxide fine particles having an average particle size of 0.05 μm were dispersed in water at 10 weight %. Subsequently, an aqueous 10 weight % solution of sodium silicate with a molar ratio, $SiO_2/Na_2O$, of 0.5, was added, which corresponds to 2 weight % of $SiO_2$ relative to the amount of the titanium oxide, and stirred sufficiently. An aqueous 10 weight % solution of aluminum sulfate was gradually added, which corresponds to 7.5 weight % of $Al_2O_3$ relative to the amount of the titanium oxide to have a hydrate of silicic acid and a hydrate of alumina deposited on the surface of the titanium oxide. After completion of the reaction, filtration, washing and drying were conducted, and the product obtained was ground with a jet mill. The product obtained was transferred to a Henschel mixer, to which 2 weight % of the compound obtained in Synthesis Example 3 was added and mixed with stirring. The mixture was subjected to a baking treatment at 130 degrees C.

Preparation Method
A: Components 1 to 5 were mixed under heating and, then, component 6 was added thereto and mixed uniformly.
B: Components 7 to 9 and 11 were dissolved under heating.
C: The mixture obtained in the step B was gradually added to the mixture obtained in the step A with stirring to emulsify. Then, the emulsion was cooled and component 10 was added thereto to obtain a cream.

The water-in-oil cream comprising the present treated powder had no stickiness or oiliness, gave moist, fresh, and refreshing feeling. In addition, the durability of makeup was excellent, the makeup did not change with time or in temperature change and, therefore, the stability was excellent.

Example 10: Water-In-Oil Cream

| (Component) | Weight (%) |
|---|---|
| 1. Alkyl-modified, cross-linked, polyether-modified silicone (Note 1) | 4.0 |
| 2. Alkyl-modified, cross-linked, dimethylpolysiloxane (Note 2) | 6.0 |
| 3. Branched silicone/alkyl, polyether-modified silicone(Note 3) | 0.5 |
| 4. Liquid paraffin | 9.0 |
| 5. Dimethylpolysiloxane, 6 $mm^2$/sec | 3.0 |
| 6. Neopentyl glycol dioctanoate, IOB = 0.32 | 5.0 |
| 7. Hybrid silicone composite powder(Note 4) | 1.5 |
| 8. Treated powder 1 | 2.0 |
| 9. Glycerin | 3.0 |
| 10. 1,3-Butylene glycol | 7.0 |
| 11. Sodium citrate | 0.2 |
| 12. Sodium chloride | 0.5 |
| 13. Antiseptic | 0.1 |
| 14. Perfume | 0.1 |
| 15. Purified water | 58.1 |

(Note 1)
Alkyl modified, cross-linked, polyether-modified silicone: KSG-310, ex Shin-Etsu Chemical Co., Ltd.
(Note 2)
Alkyl-modified, cross-linked, dimethylpolysiloxane: KSG-41, ex Shin-Etsu Chemical Co., Ltd.
(Note 3)
Branched silicone/alkyl, polyether-modified silicone: KF-6038, ex Shin-Etsu Chemical Co., Ltd.
(Note 4)
Hybrid silicone composite powder: KSP-100, ex Shin-Etsu Chemical Co., Ltd.

Preparation Method
A: Components 1 to 8 were mixed.
B: Components 9 to 13 and 15 were mixed to dissolve together.
C: The mixture obtained in the step B was added to the mixture obtained in the step A with stirring to emulsify. Then, component 14 was added thereto to obtain a water-in-oil cream.

The water-in-oil cream comprising the present treated powder had no stickiness or oiliness and gave a moist feeling. In addition, the makeup did not change with time or in temperature change and, therefore, the stability was excellent.

Example 11: Water-In-Oil Cream

| (Component) | Weight (%) |
|---|---|
| 1. Alkyl-modified, cross-linked, polyether-modified silicone (Note 1) | 6.0 |
| 2. Liquid paraffin | 10.0 |
| 3. Methylphenyl polysiloxane | 3.5 |
| 4. Glyceryl trimyristate, IOB = 0.20 | 5.0 |
| 5. Branched silicone/alkyl, polyglycerin-modified silicone(Note 2) | 0.5 |
| 6. Hybrid silicone composite powder(Note 3) | 3.0 |
| 7. Treated powder 2 | 2.0 |
| 8. Sodium citrate | 0.2 |
| 9. Propylene glycol | 8.0 |
| 10. Glycerin | 3.0 |
| 11. Antiseptic | 0.1 |
| 12. Perfume | 0.1 |
| 13. Purified water | 58.6 |

(Note 1)
Alkyl-modified, cross-linked, polyether-modified silicone: KSG-310, ex Shin-Etsu Chemical Co. Ltd.
(Note 2)
Branched silicone/alkyl, polyglycerin-modified silicone: KF-6105, ex Shin-Etsu Chemical Co. Ltd.
(Note 3)
Hybrid silicone composite powder: KSP-100, ex Shin-Etsu Chemical Co. Ltd.

Preparation Method
A: Components 1 to 7 were mixed.
B: Components 8 to 13 were mixed to dissolve together. The mixture obtained was added to the mixture obtained in the step A with stirring to emulsify.

The water-in-oil cream comprising the present treated powder had no stickiness or oiliness, gave moist, fresh, and refreshing feeling. In addition, the durability of makeup was excellent and the makeup did not change with time or in temperature change and, therefore, the stability was excellent.

Example 12: Water-In-Oil Cream

| (Component) | Weight (%) |
|---|---|
| 1. Decamethylcyclopentasiloxane | 16.0 |
| 2. Dimethylpolysiloxane, 6 $mm^2$/sec | 4.0 |
| 3. Polyether-modified silicone(Note 1) | 5.0 |
| 4. POE (5) octyldodecyl ether | 1.0 |
| 5. Polyoxyethylene sorbitan monostearate, 20 E.O. | 0.5 |
| 6. Anhydrous silicic acid-treated zinc oxide(Note 2) | 2.0 |
| 7. Treated powder 9 | 10.0 |
| 8. Liquid paraffin | 2.0 |
| 9. Glyceryl trimyristate, IOB = 0.20 | 1.0 |
| 10. *Scutellaria* extract(Note 3) | 1.0 |
| 11. *Gentiana* extract(Note 4) | 0.5 |
| 12. Ethanol | 5.0 |

-continued

| (Component) | Weight (%) |
|---|---|
| 13. 1,3-Butylene glycol | 2.0 |
| 14. Antiseptic | 0.1 |
| 15. Perfume | 0.1 |
| 16. Purified water | 50.8 |

(Note 1)
Polyether-modified silicone: KF-6017, ex Shin-Etsu Chemical Co. Ltd.
(Note 2)
Anhydrous silicic acid-treated zinc oxide: 50% zinc oxide-endohedral silica having a particle diameter of 0.01 to 10 μm, Sunsphere SZ-5, ex Asahi Glass Co., Ltd.
(Note 3)
*Scutellaria* extract: extracted with an aqueous 50% solution of 1,3-butylene glycol
(Note 4)
*Gentiana* extract: extracted with an aqueous 20% solution of ethanol Preparation Method A: Components 6 to 9 were mixed.

B: Components 1 to 5 were mixed and the mixture obtained in the step A was added thereto.

C: Components 10 to 14 and 16 was mixed and the mixture obtained in the step B was added to emulsify.

D: The mixture obtained in the step C was cooled, and component 15 was added thereto to obtain a cream.

The water-in-oil cream comprising the present treated powder spread lightly, had excellent adhesion feel, makeup was very fit and gave a glossy finish. The durability of makeup was excellent. In addition, the makeup did not change with time or in temperature change and, therefore, the stability was excellent.

Example 13: Eyeliner

| (Component) | Weight (%) |
|---|---|
| 1. Decamethylcyclopenta siloxane | 22.0 |
| 2. Dimethylpolysiloxane, 6 mm$^2$/sec | 5.0 |
| 3. Treated powder 8 | 20.0 |
| 4. Organic silicone resin(Note 1) | 10.0 |
| 5. Vitamin E acetate | 0.2 |
| 6. Isocetyl isostearate, IOB = 0.09 | 2.0 |
| 7. Bentonite | 3.0 |
| 8. Polyether-modified silicone(Note 2) | 2.0 |
| 9. Ethanol | 3.0 |
| 10. 1,3-Butylene glycol | 5.0 |
| 11. Antiseptic | 0.1 |
| 12. Purified water | 27.7 |

(Note 1)
Organic silicone resin: KF-7312J, ex Shin-Etsu Chemical Co. Ltd.
(Note 2)
Polyether-modified silicone: KF-6017, ex Shin-Etsu Chemical Co. Ltd.

Preparation Method

A: Components 1, 2 and 4 to 8 were mixed, then, component 3 was added thereto, and mixed to disperse uniformly.

B: Components 9 to 11 and 13 were mixed together.

C: The mixture obtained in the step B was gradually added to the mixture obtained in the step A and emulsified. Then, the emulsion was cooled to obtain an eyeliner.

The eyeliner comprising the present treated powder elongated lightly, tended to draw easily, gave a fresh feeling, and had no stickiness. In addition, the makeup did not change with time or in temperature change and, therefore, the stability and usability were excellent, water resistance and perspiration resistance were both excellent, and the durability of makeup was excellent.

Example 14: Eyeliner

| (Component) | Weight (%) |
|---|---|
| 1. Decamethylcyclopentasiloxane | 6.0 |
| 2. Dimethylpolysiloxane, 6 mm$^2$/sec at 25 degrees C. | 5.0 |
| 3. Isocetyl isostearate, IOB = 0.09 | 2.0 |
| 4. Polyether-modified silicone (Note 1) | 1.0 |
| 5. Branched silicone/alkyl, polyether-modified silicone (Note 2) | 1.0 |
| 6. Acrylic silicone resin(Note 3) | 15.0 |
| 7. Treated powder 7 | 20.0 |
| 8. Ethanol | 5.0 |
| 9. Antiseptic | 0.1 |
| 10. Purified water | 44.9 |

(Note 1)
Polyether-modified silicone: KF-6017, ex Shin-Etsu Chemical Co. Ltd.
(Note 2)
Branched silicone/alkyl, polyether-modified silicone: KF-6038, ex Shin-Etsu Chemical Co. Ltd.
(Note 3)
Acrylic silicone resin: KP-545, ex Shin-Etsu Chemical Co. Ltd.

Preparation Method

A: Components 1 to 6 were mixed under heating, then, component 7 was added thereto, and dispersed uniformly.

B: Components 8 to 10 were dissolved together under heating.

C: The mixture obtained in the step B was gradually added to the mixture obtained in the step A with stirring to emulsify to obtain an eyeliner.

The eyeliner comprising the present treated powder elongated lightly, had no oily or powdery feeling, gave fresh feeling in use, and had good water resistance, water repellency and perspiration resistance. The durability of makeup was excellent, the makeup did not change with time or in temperature change, and, therefore, the stability was excellent.

Example 15: Cream Eye Shadow

| (Component) | Weight (%) |
|---|---|
| 1. Acrylic silicone resin (Note 1) | 10.0 |
| 2. Long-chain alkyl-containing acrylic silicone resin (Note 2) | 2.0 |
| 3. Branched-silicone, polyether-modified silicone (Note 3) | 1.5 |
| 4. Decamethylcyclopentasiloxane | 20.3 |
| 5. Cetyl Isooctanoate, IOB = 0.13 | 3.0 |
| 6. Organic-modified bentonite | 1.2 |
| 7. Nylon powder | 3.0 |
| 8. Treated powder 10 | 4.0 |
| 9. Treated powder 7 | 20.0 |
| 10. Ethanol | 5.0 |
| 11. Antiseptic | proper quantity |
| 12. Purified water | 30.0 |

(Note 1)
Acrylic silicone resin: KP-545, ex Shin-Etsu Chemical Co. Ltd.
(Note 2)
Long-chain alkyl-containing acrylic silicone resin: KP-561P, ex Shin-Etsu Chemical Co. Ltd.
(Note 3)
Branched-silicone, polyether-modified silicone: KF-6028, ex Shin-Etsu Chemical Co. Ltd.

Preparation Method

A: Components 1 to 6 were mixed and, then, components 7 to 9 were added thereto and dispersed uniformly.

B: Components 10 to 12 were mixed together uniformly.

C: The mixture obtained in the step B was added gradually to the mixture obtained in the step A with stirring to emulsify to obtain a cream eye shadow.

The cream eye shadow comprising the present treated powder had no oily or powdery feeling, gave fresh feeling in use, and well adhered to the skin. In addition, the cream eye shadow had good water resistance, water repellency and perspiration resistance. The durability of makeup was excellent, the makeup did not change with time or in temperature change, and, therefore, the stability was excellent.

Example 16: Lipstick

| (Component) | Weight (%) |
| --- | --- |
| 1. Candelilla wax | 8.0 |
| 2. Polyethylene wax | 8.0 |
| 3. Long-chain alkyl-containing acrylic silicone resin (Note 1) | 12.0 |
| 4. Methyl phenyl polysiloxane (Note 2) | 3.0 |
| 5. Isotridecyl isononanate, IOB = 0.16 | 20.0 |
| 6. Glyceryl isostearate, IOB = 0.63 | 16.0 |
| 7. Diglyceryl triisostearate, IOB = 0.27 | 28.5 |
| 8. Treated powder 3 | 2.1 |
| 9. Treated powder 6 | 1.0 |
| 10. Treated powder 7 | 0.2 |
| 11. Treated powder 1 | 1.0 |
| 12. Antiseptic | 0.1 |
| 13. Perfume | 0.1 |

(Note 1)
Long-chain alkyl-containing acrylic silicone resin: KP-561P, ex Shin-Etsu Chemical Co. Ltd.
(Note 2)
Methyl phenyl polysiloxane: KF-54, ex Shin-Etsu Chemical Co. Ltd.

Preparation Method
A: Components 1 to 6 and a part of component 7 were mixed under heating to dissolve together.
B: Components 8 to 13 and the rest of component 7 were mixed uniformly. The mixture obtained was added to the mixture obtained in the step A and mixed uniformly.

The lipstick obtained had no oily or powdery feeling, gave fresh feeling in use, had good water resistance, water repellency and perspiration resistance. The durability of makeup was good and the stability was excellent.

Example 17: Emulsion Liquid Foundation

| (Component) | Weight (%) |
| --- | --- |
| 1. Methylpolysiloxane, 6 mm$^2$/sec at 25 degrees C. | 4.5 |
| 2. Decamethylcyclopentasiloxane | 15.0 |
| 3. Squalane | 4.0 |
| 4. Neopentyl glycol dioctanoate, IOB = 0.32 | 3.0 |
| 5. Diglyceryl myristate isostearate, IOB = 0.45 | 2.0 |
| 6. α-diisostearyl glyceryl ether, IOB = 0.18 | 1.0 |
| 7. Polyether-modified silicone (Note 1) | 1.0 |
| 8. Branched silicone/alkyl, polyether-modified silicone (Note 2) | 0.5 |
| 9. Treated powder 2 | 5.0 |
| 10. Treated powder 11 | 2.0 |
| 11. Treated powder 10 | 3.0 |
| 12. Treated powder 4 | 0.4 |
| 13. Treated powder 6 | 0.7 |
| 14. Treated powder 8 | 0.1 |
| 15. Magnesium sulfate | 0.7 |
| 16. Glycerin | 3.0 |
| 17. Antiseptic | 0.1 |
| 18. Perfume | 0.1 |
| 19. Purified water | 53.8 |

(Note 1)
Polyether-modified silicone: KF-6017, ex Shin-Etsu Chemical Co. Ltd.
(Note 2)
Branched silicone/alkyl, polyether-modified silicone: KF-6105, ex Shin-Etsu Chemical Co. Ltd.

Preparation Method
A: Components 4 and 8 were mixed and, then, components 9 to 14 were added thereto and dispersed uniformly.
B: Components 1 to 3 and 5 to 7 were mixed together.
C: Components 15 to 17 and 19 were mixed together.
D: The mixture obtained in the step A was added to the mixture obtained in the step B with stirring and mixed uniformly, the mixture obtained in the step C was added thereto and emulsified, and, then, component 18 was added to obtain an emulsion liquid foundation.

The emulsion liquid foundation comprising the present treated powder had a low viscosity and a fine texture, spread lightly, had no stickiness or oiliness, gave moist, fresh, and refreshing feeling in use. In addition, the durability of makeup was excellent, the makeup did not change with time or in temperature change, and, therefore, the stability was excellent.

Example 18: Oil-In-Water Liquid Foundation

| (Component) | Weight (%) |
| --- | --- |
| 1. Stearic acid | 1.0 |
| 2. Behenyl alcohol | 0.4 |
| 3. Glyceryl stearate, IOB = 0.62 | 0.3 |
| 4. Liquid paraffin | 10.0 |
| 5. Glyceryl trioctanoate, IOB = 0.35 | 5.0 |
| 6. Long-chain alkyl-containing acrylic silicone resin (Note 1) | 3.0 |
| 7. Sorbitan sesquioleate | 0.5 |
| 8. Sorbitan monooleate | 1.0 |
| 9. Acrylic/alkyl copolymer | 2.2 |
| 10. Triethanolamine | 1.0 |
| 11. Ethanol | 3.0 |
| 12. Hybrid silicone composite powder (Note 2) | 3.0 |
| 13. Polyether-modified silicone (Note 3) | 0.2 |
| 14. Alkyl/POE palmityl ether phosphate | 0.1 |
| 15. POE hydrogenated castor oil | 0.5 |
| 16. Treated powder 2 | 8.5 |
| 17. Treated powder 4 | 0.4 |
| 18. Treated powder 5 | 1.0 |
| 19. Treated powder 8 | 0.1 |
| 20. 1,3-Butylene glycol | 7.0 |
| 21. Antiseptic | 0.1 |
| 22. Perfume | 0.1 |
| 23. Purified water | 51.6 |

(Note 1)
Long-chain alkyl-containing acrylic silicone resin: KP-561P, ex Shin-Etsu Chemical Co. Ltd.
(Note 2)
Hybrid silicone composite powder: KSP-100, ex Shin-Etsu Chemical Co. Ltd.
(Note 3)
Polyether-modified silicone: KF-6013, ex Shin-Etsu Chemical Co. Ltd.

Preparation Method
A: Components 13 to 15 and a part of component 20 were mixed and, then, components 16 to 19 were added thereto, dispersed uniformly and heated.
B: Components 1 to 8 were mixed to dissolve together uniformly under heating.
C: Components 9, 10, the rest of component 20, and components 21 and 23 were mixed and heated.
D: Components 11 to 12 were mixed together.
E: The mixture obtained in the step B was added to the mixture obtained in the step C with stirring to emulsify, the mixture obtained in the step A was added thereto, and further the mixture obtained in the step D and component 22 were added thereto to obtain an oil-in-water liquid foundation.

The oil-in-water liquid foundation obtained had no stickiness, gave moist, fresh, and a beautiful cosmetic film, and had water resistance, water repellency and perspiration resistance. The durability of makeup was excellent, the makeup did not change with time or in temperature change, and, therefore, the stability was excellent.

Example 19: Water-In-Oil Cream Foundation

| (Component) | Weight (%) |
| --- | --- |
| 1. Alkyl-modified cross-linked, polyether-modified silicone (Note 1) | 2.0 |
| 2. Alkyl-modified cross-linked, dimethyl polysiloxane (Note 2) | 2.0 |
| 3. Branched silicone/alkyl, polyether silicone (Note 3) | 1.0 |
| 4. Liquid paraffin | 2.0 |
| 5. Glyceryl trioctanoate, IOB = 0.35 | 5.0 |
| 6. Isotridecyl isononanoate, IOB = 0.16 | 9.0 |
| 7. Lecithin | 0.3 |
| 8. Polysorbate 80 | 0.3 |
| 9. Hybrid silicone composite powder (Note 4) | 2.0 |
| 10. Treated powder 1 | 8.5 |
| 11. Treated powder 3 | 0.4 |
| 12. Treated powder 5 | 1.0 |
| 13. Treated powder 7 | 0.1 |
| 14. 1,3-Butylene glycol | 5.0 |
| 15. Sodium citrate | 0.2 |
| 16. Sodium chloride | 0.5 |
| 17. Antiseptic | 0.1 |
| 18. Perfume | 0.1 |
| 19. Purified water | 60.4 |

(Note 1)
Alkyl-modified cross-linked, polyether-modified silicone: KSG-310, ex Shin-Etsu Chemical Co. Ltd.
(Note 2)
Alkyl-modified cross-linked, dimethyl polysiloxane: KSG-41, ex Shin-Etsu Chemical Co. Ltd.
(Note 3)
Branched silicone/alkyl, polyether silicone: KF-6038, ex Shin-Etsu Chemical Co. Ltd.
(Note 4)
Hybrid silicone composite powder: KSP-300, ex Shin-Etsu Chemical Co. Ltd.

Preparation Method
A: Components 7 to 9 and 15 were mixed, then, components 10 to 13 were added thereto, and the mixture was dispersed in a part of component 14.
B: Components 1 to 6 were mixed together uniformly.
C: Components 16 to 18 and the rest of component 14 were mixed together.
D: The mixture obtained in the step C was added to the mixture obtained in the step B with stirring to emulsify, and the mixture obtained in the step A and component 19 were added thereto to obtain a water-in-oil cream foundation.

The water-in-oil cream foundation obtained spread lightly, gave a powdery makeup, had no stickiness, gave moist, fresh, and a beautiful cosmetic film, and had water resistance, water repellency and perspiration resistance. The durability of makeup was excellent, the makeup did not change with time or in temperature change, and, therefore, the stability was excellent.

Example 20: Water-In-Oil Compact Foundation

| (Component) | Weight (%) |
| --- | --- |
| 1. Ceresin | 5.5 |
| 2. Microcrystalline wax | 1.0 |
| 3. Neopentyl glycol dioctanoate, IOB = 0.32 | 8.0 |
| 4. Glyceryl trioctanoate, IOB = 0.35 | 4.0 |
| 5. Decamethylcyclopentasiloxane | 6.0 |
| 6. Dimethylpolysiloxane, 6 mm$^2$/sec at 25 degree C. | 6.0 |
| 7. Cross-linked, polyether-modified silicone (Note 1) | 4.0 |
| 8. Branched silicone/alkyl, polyether silicone (Note 2) | 1.2 |
| 9. Sorbitan tetraisostearate | 1.0 |
| 10. Glycerin | 0.5 |
| 11. Treated powder 2 | 8.5 |
| 12. Treated powder 4 | 0.4 |
| 13. Treated powder 6 | 1.0 |
| 14. Treated powder 8 | 0.1 |
| 15. 1,3-Butylene glycol | 5.0 |
| 16. Sodium citrate | 0.2 |
| 17. Antiseptic | 0.1 |
| 18. Perfume | 0.1 |
| 19. Purified water | 47.4 |

(Note 1)
Cross-linked, polyether-modified silicone: KSG-210, ex Shin-Etsu Chemical Co. Ltd.
(Note 2)
Branched silicone/alkyl, polyether silicone: KF-6038, ex Shin-Etsu Chemical Co. Ltd.

Preparation Method
A: Components 9 to 10 and 4 were mixed, then, components 11 to 14 were added thereto and dispersed uniformly and heated.
B: Components 1 to 3 and 5 to 8 were mixed uniformly under heating.
C: Components 15 to 17 and 19 were mixed and heated.
D: The mixture obtained in the step A was added to the mixture obtained in the step B and mixed uniformly, the mixture obtained in the step C was added thereto to emulsify, component 18 was added thereto, and the mixture was poured into a container to obtain a water-in-oil compact foundation.

The water-in-oil compact foundation comprising the present treated powder gave a dry finish feeling, had no stickiness, gave moist, fresh, and a beautiful cosmetic film, and had water resistance, water repellency and perspiration resistance. The durability of makeup was excellent, the makeup did not change with time or in temperature change, and, therefore, the stability was excellent.

Example 21: Water-In-Oil Stick Foundation

| (Component) | Weight (%) |
| --- | --- |
| 1. Ceresin | 5.5 |
| 2. Stearoyl Inulin (Note 1) | 2.0 |
| 3. Neopentyl glycol dioctanoate, IOB = 0.32 | 8.0 |
| 4. Glyceryl trioctanoate, IOB = 0.35 | 5.0 |
| 5. Dimethylpolysiloxane, 6 mm$^2$/sec at 25 degrees C. | 11.5 |
| 6. Cross-linked polyglycerin-modified silicone (Note 2) | 4.0 |
| 7. Branched silicone/alkyl, polyglycerin-modified silicone (Note 3) | 1.5 |
| 8. Spherical polymethylsilsesquioxane powder (Note 4) | 1.5 |
| 9. Lecithin | 0.2 |
| 10. POE sorbitan monooleate | 0.3 |
| 11. Treated powder 1 | 8.5 |
| 12. Treated powder 3 | 0.4 |
| 13. Treated powder 5 | 1.0 |
| 14. Treated powder 7 | 0.1 |
| 15. Dipropylene glycol | 5.0 |
| 16. Sodium citrate | 0.2 |
| 17. Sodium chloride | 0.5 |
| 18. Antiseptic | 0.1 |

-continued

| (Component) | Weight (%) |
|---|---|
| 19. Perfume | 0.1 |
| 20. Purified water | 44.6 |

(Note 1)
Stearoyl Inulin: Rheopearl ISK, ex Chiba Flour Milling Co. Ltd.
(Note 2)
Cross-linked, polyglycerin-modified silicone: KSG-710, ex Shin-Etsu Chemical Co. Ltd.
(Note 3)
Branched silicone/alkyl, polyglycerin-modified silicone: KF-6105, ex Shin-Etsu Chemical Co. Ltd.
(Note 4)
Spherical polymethylsilsesquioxane powder: KMP-590, ex Shin-Etsu Chemical Co. Ltd.

Preparation Method
A: Components 9, 10 and 15 were mixed, components 11 to 14 were added thereto and dispersed uniformly and the mixture was dispersed in a part of component 20 and heated.
B: Components 1 to 8 were mixed together uniformly under heating.
C: Components 16 to 18 and the rest of component 20 were mixed together and heated.
D: The mixture obtained in the step C was added to the mixture obtained in the step B with stirring to emulsify, the mixture obtained in the step A was added thereto, then, component 19 was added thereto and the mixture was poured into a container to obtain a water-in-oil stick foundation.

The water-in-oil stick foundation obtained spread lightly, gave a dry finish feeling, had no stickiness, gave moist, fresh, and a beautiful cosmetic film, and had water resistance, water repellency and perspiration resistance. The durability of makeup was excellent, the makeup did not change with time or in temperature change, and, therefore, the stability was excellent.

Example 22: Hair Treatment Agent

| (Component) | Weight (%) |
|---|---|
| 1. Ethylene glycol distearate, IOB = 0.16 | 1.0 |
| 2. Liquid paraffin | 10.0 |
| 3. Squalane | 5.0 |
| 4. Stearyl alcohol | 1.5 |
| 5. Dimethylpolysiloxane, 10 mm²/sec at 25 degrees C. | 3.0 |
| 6. Stearic acid | 6.0 |
| 7. Polyoxyethylene (3) stearyl alcohol | 4.5 |
| 8. Polyoxyethylene (150) cetyl ether | 2.0 |
| 9. Treated powder 11 | 1.5 |
| 10. 1,3-Butylene glycol | 6.0 |
| 11. Antiseptic | 0.1 |
| 12. Perfume | 0.1 |
| 13. Purified water | 59.3 |

Preparation Method
A: Components 1 to 8 were mixed under heating, and components 9 was added thereto and mixed uniformly.
B: Components 10, 11 and 13 were mixed to prepare a dispersion.
C: The dispersion obtained in the step B was added to the mixture obtained in the step A and mixed, the mixture was cooled, and component 12 was added to the mixture to obtain a hair treatment agent.

The hair treatment agent obtained had no stickiness or heavy feeling in use, gave an excellent glaze, a dry feeling, a smoothness and a sense of volume on hair, made it easy to comb hair, and had excellent usability and durability of makeup.

Example 23: Water-In-Oil Type Antiperspirant

| (Component) | Weight (%) |
|---|---|
| 1. Cross-linked, polyether-modified silicone (Note 1) | 7.0 |
| 2. Decamethylcyclopentasiloxane | 10.0 |
| 3. Glyceryl trioctanoate, IOB = 0.35 | 7.0 |
| 4. Dipropylene glycol | 5.0 |
| 5. Sodium citrate | 0.2 |
| 6. Aluminum zirconium tetrachlorohydrate | 18.0 |
| 7. Treated powder 9 | 5.0 |
| 8. Phenyl-modified, hybrid silicone composite powder (Note 2) | 2.0 |
| 9. Perfume | 0.1 |
| 10. Purified water | 45.7 |

(Note 1)
Cross-linked, polyether-modified silicone: KSG-210, ex Shin-Etsu Chemical Co. Ltd.
(Note 2)
Phenyl-modified, hybrid silicone composite powder: KSP-300, ex Shin-Etsu Chemical Co. Ltd.

Preparation Method
A: Components 1 to 3 were mixed.
B: Components 4 to 10 were mixed together.
C: The mixture obtained in the step B was added to the mixture obtained in the step A, mixed to emulsify.

The water-in-oil type antiperspirant obtained had refreshing feeling, and had no stickiness or oiliness. The makeup did not change with time or in temperature change, and the usability and the stability were excellent.

Example 24: Roll-On Type Antiperspirant

| (Component) | Weight (%) |
|---|---|
| 1. Cross-linked, polyether-modified silicone (Note 1) | 20.0 |
| 2. Cross-linked dimethylpolysiloxane (Note 2) | 15.0 |
| 3. Dimethylpolysiloxane, 6 mm²/sec at 25 degrees C. | 10.0 |
| 4. Decamethylcyclopentasiloxane | 30.0 |
| 5. Aluminum zirconium tetrachlorohydrate | 20.0 |
| 6. Treated powder 9 | 4.9 |
| 7. Perfume | 0.1 |

(Note 1)
Cross-linked, polyether-modified silicone: KSG-210, ex Shin-Etsu Chemical Co. Ltd.
(Note 2)
Cross-linked dimethylpolysiloxane: KSG-15, ex Shin-Etsu Chemical Co. Ltd.

Preparation Method
A: Components 1 to 4 were mixed uniformly.
B: Components 5 to 7 were added to the mixture obtained in the step A and dispersed uniformly.

The roll-on type antiperspirant obtained had refreshing feeling, and had no stickiness or oiliness. The makeup did not change with time or in temperature change, and, the usability and the stability were excellent.

Example 25: Sunscreen Emulsion

| (Component) | Weight (%) |
|---|---|
| 1. Decamethylcyclopentasiloxane | 20.0 |
| 2. Methylphenyl polysiloxane | 3.0 |
| 3. Sorbitan monoisostearate | 1.0 |

-continued

| (Component) | Weight (%) |
| --- | --- |
| 4. Polyether-modified silicone (Note 1) | 1.5 |
| 5. Trimethylsiloxy silicic acid (Note 2) | 1.0 |
| 6. Octyl p-methoxy cinnamate, IOB = 0.28 | 4.0 |
| 7. Treated powder 9 | 8.0 |
| 8. Sorbitol | 2.0 |
| 9. Sodium chloride | 2.0 |
| 10. Antiseptic | 0.1 |
| 11. Perfume | 0.1 |
| 12. Purified water | 55.3 |

(Note 1)
Polyether-modified silicone: KF-6015, ex Shin-Etsu Chemical Co. Ltd.
(Note 2)
Trimethylsiloxy silicic acid: X-21-5250, ex Shin-Etsu Chemical Co. Ltd.

Preparation Method

A: Components 1 to 6 were mixed under heating and component 7 was added thereto and dispersed uniformly.
B: Components 8 to 10 and 12 were mixed together under heating.
C: The mixture obtained in the step B was gradually added to the mixture obtained in the step A and emulsified, the emulsion was cooled, and component 11 was added thereto to obtain a sunscreen lotion.

The sunscreen lotion obtained spread lightly, had no stickiness or oiliness, and had moisture and fresh feeling. The durability of makeup was excellent, so that the effect of protection from UV could last long, the makeup did not change with time or in temperature change, and the stability was excellent.

Example 26: Water-In-Oil Sunscreen Cream

| (Component) | Weight (%) |
| --- | --- |
| 1. Cross-linked, polyether-modified silicone (Note 1) | 3.0 |
| 2. Cross-linked dimethyl polysiloxane (Note 2) | 6.0 |
| 3. Branched silicons/alkyl, polyether-modified silicone (Note 3) | 1.0 |
| 4. Neopentyl glycol dioctanoate, IOB = 0.32 | 9.0 |
| 5. Octyl p-methoxy cinnamate, IOB = 0.28 | 5.0 |
| 6. Titanium oxide fine particle dispersion (Note 4) | 5.0 |
| 7. Treated powder 9 | 18.0 |
| 8. Alkyl polyglycerin-modified, branched silicone (Note 5) | 1.5 |
| 9. Decamethylcyclopentasiloxane | 10.5 |
| 10. Acrylic silicone resin (Note 6) | 12.0 |
| 11. Silica | 0.2 |
| 12. Pentylene glycol | 7.0 |
| 13. Sodium citrate | 0.2 |
| 14. Sodium chloride | 0.5 |
| 15. Perfume | 0.1 |
| 16. Purified water | 21.0 |

(Note 1)
Cross-linked, polyether-modified silicone: KSG-240, ex Shin-Etsu Chemical Co. Ltd.
(Note 2)
Cross-linked dimethyl polysiloxane: KSG-15, ex Shin-Etsu Chemical Co. Ltd.
(Note 3)
Branched silicone/alkyl, polyether-modified silicone: KF-6038, ex Shin-Etsu Chemical Co. Ltd.
(Note 4)
Titanium oxide fine particle dispersion: SPD-T5, ex Shin-Etsu Chemical Co. Ltd.
(Note 5)
Alkyl polyglycerin-comodified, branched silicone: KF-6105, ex Shin-Etsu Chemical Co. Ltd.
(Note 6)
Acrylic silicone resin: KP-545, ex Shin-Etsu Chemical Co. Ltd.

Preparation Method

A: Components 8 and 9 were mixed uniformly, and component 7 was added thereto and dispersed with a beads mill.
B: Components 1 to 5 and 10 to 11 were mixed together uniformly.
C: Components 12 to 14 and 16 were mixed together uniformly.
D: The mixture obtained in the step A and component 6 were gradually added to the mixture obtained in the step B and mixed uniformly, the mixture obtained in the step C was added thereto to emulsify, and component 15 was added thereto to obtain a water-in-oil sunscreen cream.

The water-in-oil sunscreen cream obtained had no stickiness, spread lightly, and had good adhesiveness and fitness on the skin. The makeup did not become white on the skin, had a glossy finish, the durability of makeup was excellent so that the effect of protection from UV could last long, and the makeup was stable with time or in a temperature change.

Example 27: Oil-In-Water Sunscreen Cream

| (Component) | Weight (%) |
| --- | --- |
| 1. Cross-linked, methyl phenyl polysiloxane (Note 1) | 5.0 |
| 2. Cetyl Isooctanoate, IOB = 0.13 | 7.0 |
| 3. Titanium oxide fine particles (Note 2) | 6.0 |
| 4. Decamethylcyclopentasiloxane | 8.0 |
| 5. Branched-silicone polyether-modified silicone (Note 3) | 1.0 |
| 6. Polyether-modified silicone (Note 4) | 1.0 |
| 7. Acrylic acid amide mixture (Note 5) | 2.0 |
| 8. Propylene glycol | 5.0 |
| 9. Methylcellulose (aqueous 2% solution) (Note 6) | 5.0 |
| 10. Antiseptic | 0.1 |
| 11. Perfume | 0.1 |
| 12. Purified water | 59.8 |

(Note 1)
Cross-linked, methyl phenyl polysiloxane: KSG-18A, ex Shin-Etsu Chemical Co. Ltd.
(Note 2)
95 Parts of titanium oxide fine particles were added to a reactor. A solution, in toluene, of 3 parts of the compound obtained in Synthesis Example 1 and 2 parts of the compound obtained in Synthesis Example 2, which were treating agents for organopolysiloxane powder was gradually added to the reactor with stirring. The toluene was distilled off and the obtained product was subjected to a baking treatment at 150 degrees C. for 3 hours.
(Note 3)
Silicone-branched, polyether-modified silicone: KF-6028, ex Shin-Etsu Chemical Co. Ltd.
(Note 4)
Polyether-modified silicone: KF-6011, ex Shin-Etsu Chemical Co. Ltd.
(Note 5)
Acrylic acid amide-based mixture: Sepigel 305, ex Seppic
(Note 6)
Methylcellulose: Metolose SM-4000, ex Seppic Preparation Method A: Components 3 to 5 were mixed uniformly.
B: Components 1 and 2 were mixed together uniformly, and the mixture obtained in the step A was added and mixed uniformly.
C: Components 6 to 10 and 12 were mixed together uniformly.
D: The mixture obtained in the step B was gradually added to the mixture obtained in the step C and emulsified, and component 11 was added thereto to obtain an oil-in-water sunscreen cream.

The oil-in-water sunscreen cream obtained spread lightly, had no stickiness or oiliness and was transparent. The durability of makeup was excellent so that the effect of protection from UV could be last long, and the makeup was stable with time or in a temperature change.

Example 28: W/O/W Type Cream

| (Component) | Weight (%) |
|---|---|
| 1. Cross-linked, polyether-modified silicone (Note 1) | 5.0 |
| 2. Cetyl Isooctanoate, IOB = 0.13 | 5.0 |
| 3. Alkyl-modified, cross-linked dimethylpolysiloxane (Note 2) | 1.0 |
| 4. Methyl trimethicone (Note 3) | 5.0 |
| 5. Methyl glucose dioleate | 1.5 |
| 6. Isohexadecane | 3.5 |
| 7. Magnesium sulfate | 0.5 |
| 8. Propylene glycol | 5.0 |
| 9. Purified water | 39.5 |
| 10. Cetyl alcohol | 1.0 |
| 11. PEG-10 soya sterol | 2.0 |
| 12. Treated powder 10 | 0.5 |
| 13. Antiseptic | 0.1 |
| 14. Perfume | 0.1 |
| 15. Purified water | 30.3 |

(Note 1) Cross-linked, polyether-modified silicone: KSG-210, ex Shin-Etsu Chemical Co. Ltd.
(Note 2) Alkyl-modified, cross-linked dimethylpolysiloxane: KSG-43, ex Shin-Etsu Chemical Co. Ltd.
(Note 3) Methyl trimethicone: TMF-1.5, ex Shin-Etsu Chemical Co. Ltd.

Preparation Method

A: Components 7 to 9 were mixed.

B: Components 1 to 6 were mixed uniformly, and the mixture obtained in the step A was added, stirred to emulsify.

C: Components 10 to 13 and 15 were heated, mixed uniformly, and the mixture obtained in the step B was added with stirring to emulsify.

D: Component 14 was added to the mixture obtained in the step C and mixed uniformly to obtain a W/O/W type cream.

The W/O/W type cream obtained had a fresh feeling, had no stickiness or oiliness, and was transparent. The durability of makeup was excellent, the makeup did not change with time or in temperature change, and the stability was excellent.

Example 29: O/W/O Type Emulsion

| (Component) | Weight (%) |
|---|---|
| 1. Cross-linked, polyether-modified silicone (Note 1) | 3.0 |
| 2. Glyceryl triisooctanoate | 10.0 |
| 3. Dimethylpolysiloxane, 6 mm$^2$/sec | 5.0 |
| 4. Cross-linked dimethylpolysiloxane (Note 2) | 5.0 |
| 5. Sucrose monostearate | 3.0 |
| 6. Glycerin | 5.0 |
| 7. 1,3-Butylene glycol | 5.0 |
| 8. Treated powder 11 | 0.5 |
| 9. Antiseptic | 0.1 |
| 10. Purified water | 59.8 |
| 11. Macadamia nut oil (IOB calculation was impossible) | 2.0 |
| 12. Cetyl alcohol | 2.0 |
| 13. Perfume | 0.1 |

(Note 1) Cross-linked, polyether-modified silicone: KSG-210, ex Shin-Etsu Chemical Co. Ltd.
(Note 2) Cross-linked dimethylpolysiloxane: KSG-15, ex Shin-Etsu Chemical Co. Ltd.

Preparation Method

A: Components 1 to 4 were mixed.

B: Components 5 to 10 were mixed under heating and made uniform.

C: Components 11 and 12 were mixed under heating.

D: The mixture obtained in the step C was added to the mixture obtained in the step B with stirring, emulsified and cooled.

E: The mixture obtained in the step D was added to the mixture obtained in the step A with stirring to emulsify, component 13 was added thereto to obtain an O/W/O type emulsion.

The O/W/O type emulsion obtained had a fresh feeling, had no stickiness or oiliness, and was transparent. The durability of makeup was excellent, the makeup did not change with time or in temperature, and the stability and usability were excellent.

INDUSTRIAL APPLICABILITY

The cosmetic comprising the present surface-treated powder has an excellent adhesion and forms a uniform cosmetic film which has no unevenness in color and a good coloring property. The present cosmetic does not run with time, does not have stickiness, and gives a good feeling in use. Further, the powder disperses stably to provide a cosmetic which changes less with time. These effects are achieved even in a cosmetic comprising a mixture of a silicone oil and a polar oil. Accordingly, the surface-treated powder of the present invention can be successfully used in cosmetics.

The invention claimed is:

1. A surface-treated powder, wherein at least one compound represented by the following general formula (1) adheres to the surface of the powder,

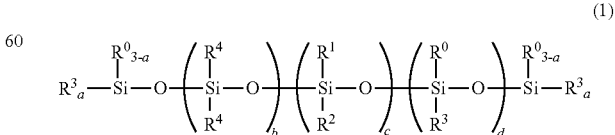

(1)

wherein R$^2$ is, independently of each other, a monovalent aromatic hydrocarbon group having 6 to 12 carbon atoms, $R^4$ is, independently of each other, a substituted or unsubstituted, monovalent non-aromatic hydrocarbon group having 1 to 30 carbon atoms, $R^1$ and $R^0$ are, independently of each other, a group selected from aforementioned groups defined for $R^2$ and $R^4$, and $R^3$ is, independently of each other, a group represented by the following formula (2):

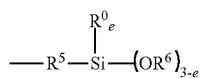
(2)

wherein $R^0$ is as defined above, $R^5$ is a divalent hydrocarbon group having 2 to 8 carbon atoms and $R^6$ is an alkyl group having 1 to 6 carbon atoms,
a is an integer of from 0 to 3, b is an integer of from 0 to 200, c is an integer of from 1 to 150, d is an integer of from 0 to 50, provided that when a is 0, d is an integer of from 1 to 50, e is an integer of from 0 to 2 and c/(b+c+d) is 0.25 or more, and the compound may or may not be a block copolymer.

2. The surface-treated powder according to claim 1, wherein the powder is at least one selected from the group consisting of powder of a surfactant metal salt, colored pigments, pearl pigments, metal powder pigments, natural colorants and other inorganic or organic powder.

3. The surface-treated powder according to claim 2, wherein the powder is zinc oxide, titanic oxide, or an extender pigment selected from the group consisting of mica, sericite, talc, and kaolin.

4. A cosmetic comprising (A) the surface-treated powder according to claim 1, and (B) oil.

5. The cosmetic according to claim 4, wherein component (B) comprises oil having an inorganic/organic balance (IOB) of 0.05 to 1.

6. The cosmetic according to claim 5, wherein the oil is a silicone oil.

7. The cosmetic according to claim 4, wherein component (B) is a mixture of the silicone oil and a polar oil other than the silicone oil having an IOB of 0.05 to 1.

8. The cosmetic according to claim 4, further comprising an organo ultraviolet absorbent.

9. The cosmetic according to claim 4, further comprising a silicone surfactant represented by the following general formula (3):

wherein R is, independently of each other, a substituted or unsubstituted, monovalent hydrocarbon group having 1 to 30 carbon atoms, and $R^7$ is, independently of each other, represented by the following formula (4) or (5), wherein an oxyethylene unit or an oxypropylene unit in the following formula (4) may or may not be a block copolymer, and a glycerin residue in the following formula (5) may have a branched structure to constitute an isomer,

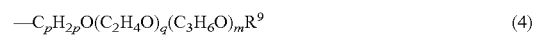 (4)

 (5)

wherein $R^8$ is a monovalent hydrocarbon group having 6 to 30 carbon atoms, $R^9$, $R^{10}$ and $R^{11}$ are, independently of each other, a hydrogen atom or a monovalent hydrocarbon group having 1 to 6 carbon atoms, and at least one of $R^{10}$ and $R^{11}$ is a hydrogen atom, f is an integer of from 0 to 200, g is an integer of from 1 to 30, h is an integer of from 0 to 50, i is an integer of from 0 to 30, p is an integer of from 1 to 6, k is an integer of from 0 to 100, q is an integer of from 0 to 50, m is an integer of from 0 to 50, provided that a total of q and m is 1 or more, and n is an integer of from 1 to 6.

10. The cosmetic according to claim 4, further comprising an acryl-silicone graft copolymer.

11. The cosmetic according to claim 4, wherein the cosmetic is any one of skin-care cosmetics, makeup cosmetics, hair cosmetics, antiperspirant cosmetics, and ultraviolet protectants.

12. The cosmetic according to claim 4, wherein the cosmetic is a water-in-oil type emulsion, an oil-in-water type emulsion, a nonaqueous cosmetic or a powder cosmetic.

13. The surface-treated powder according to claim 2, wherein the natural colorants are selected from the group consisting of carminic acid, laccaic acid, carthamin, brazilin, and crocin.

* * * * *

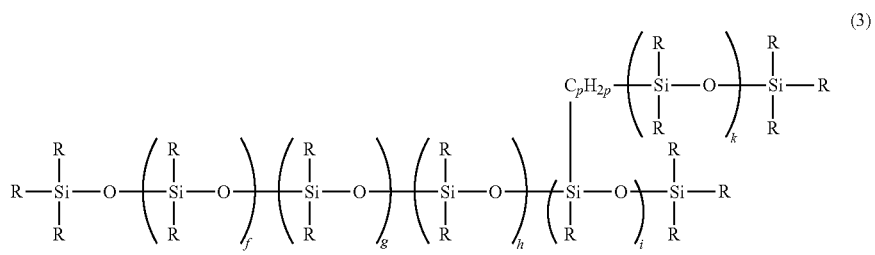
(3)